US005763217A

United States Patent [19]
Cynader et al.

[11] Patent Number: 5,763,217
[45] Date of Patent: Jun. 9, 1998

[54] METHOD OF USING, PROCESS OF PREPARING AND COMPOSITION COMPRISING RECOMBINANT HERPESVIRUS VECTORS

[75] Inventors: Max Cynader; Francis Tufaro, both of Vancouver, Canada

[73] Assignee: University of British Columbia, Vancouver, Canada

[21] Appl. No.: 540,692

[22] Filed: Oct. 11, 1995

Related U.S. Application Data

[63] Continuation-in-part of PCT/US94/12996 Nov. 10, 1994, is a continuation of Ser. No. 150,475, Nov. 10, 1993, abandoned.

[51] Int. Cl.[6] .............................. C12N 5/10; C12N 15/11; C12N 15/86; C12P 21/00

[52] U.S. Cl. ..................... 435/69.1; 435/320.1; 435/325; 435/172.5; 536/23.1; 536/24.1

[58] Field of Search ............................. 435/320.1, 240.1, 435/240.2, 172.3, 325, 69.1; 424/93.2, 93.21; 514/44; 536/23.1, 24.1

[56] References Cited

U.S. PATENT DOCUMENTS

| | | | |
|---|---|---|---|
| 4,769,331 | 9/1988 | Roizman et al. | 435/172.3 X |
| 4,859,587 | 8/1989 | Roizman | 435/68 |
| 5,288,641 | 2/1994 | Roizman | 424/199.1 |
| 5,328,688 | 7/1994 | Roizman | 424/205.1 |

FOREIGN PATENT DOCUMENTS

| | | |
|---|---|---|
| 453 242 A1 | 10/1991 | European Pat. Off. . |
| WO 90/09441 | 8/1990 | WIPO . |
| WO 91/02788 | 3/1991 | WIPO . |
| WO 92/07945 | 5/1992 | WIPO . |
| WO 93/19591 | 10/1993 | WIPO . |
| WO 94/04695 | 3/1994 | WIPO . |
| WO 94/14971 | 7/1994 | WIPO . |
| WO 95/04139 | 2/1995 | WIPO . |

OTHER PUBLICATIONS

Roizman et al. in Fields et al., eds., *Fundamental Virology* (New York: Raven Press, 1991), pp. 841-847.

"Report and Recommendations of the Panel to Assess the NIH Investment in Research on Gene Therapy," Orkin and Motulsky, Co-chairs, Dec. 7, 1995.

Altschul et al., "Basic Local Alignment Search Tool," *J. Mol. Biol. 215*:403-410, 1990.

Devereux et al., "A comprehensive set of sequence analysis programs for the VAX," *Nucleic Acids Research 12*(1):387-395, 1984.

Ishiguro et al., "Neuron-specific Expression of the Human Dopamine β-Hydroxylase Gene Requires Both the cAMP--Response Element and a Silencer Region," *Journal of Biological Chemistry 268*(24):17987-17994, 1993.

Kraner et al., "Silencing the Type II Sodium Channel Gene: A Model for Neural-Specific Gene Regulation," *Neuron 9*:37-44, 1992.

Li et al., "A cell type-specific silencer in the human choline acetyltransferase gene requiring two distinct and interactive E boxes," *Molecular Brain Research 30*:106-114, 1995.

Li et al., "Cholinergic Neuron-Specific Expression of the Human Choline Acetyltransferase Gene Is Controlled by Silencer Elements," *Journal of Neurochemistry 61*:748-751, 1993.

Li et al., "Identification of a functional silencer element involved in neuron-specific expression of the synapsin I gene," *Proc. Natl. Acad. Sci. USA 90*: 1460-1464, 1993.

Mori et al., "A Common Silencer Elements in the SCG10 and Type II $Na^+$ Channel Genes Binds a Factor Present in Nonneuronal Cells but Not in Neuronal Cells," *Neuron 9*:45-54, 1992.

Pathak et al., "The presence of both negative and positive elements in the 5'-flanking sequence of the rat Na,K-ATPase α3 subunit gene are required for brain expression in transgenic mice," *Nucleic Acid Research 22*(22):4748-4755, 1994.

Schoenherr and Anderson, "The Neuron-Restrictive Silencer Factor (NRSF): A Coordinate Repressor of Multiple Neuron-Specific Gene," *Science 267*: 1360-1363, 1995.

Brinbaumer et al., "Receptor-effector coupling by G proteins," *Biochimica et Biophysica Acta 1031*: 163-224, 1990.

Cotechhia et al., "Molecular cloning and expression of the cDNA for the hamster $\alpha_1$-adrenergic receptor," *Proc. Natl. Acad. Sci. USA 85*: 7159-63, 1988.

Schwinn et al., "Molecular Cloning and Expression of the cDNA for a Novel $\alpha_1$-Adrenergic Receptor Subtype," *Journal of Biological Chemistry 265*(14):8183-89, 1990.

Kobilka et al., "Cloning, Sequencing, and Expression of the Gene Coding for the Human Platelet $\alpha_2$-Adrenergic Receptor," *Science 238*: 650-56, 1987.

Lomasney et al., "Expansion of the $\alpha_2$-adrenergic receptor family: Cloning and characterization of human $\alpha_2$-adrenergic receptor subtype, the gene for which is located on chromosome 2," *Proc. Natl. Acad. Sci. USA 87*:5094-98, 1990.

Regan et al., "Cloning and expression of human kidney cDNA for an $\alpha_2$-adrenergic receptor subtype," *Proc. Natl. Acad. Sci. 85*:6301-6305, 1988.

Weinshank et al., "Cloning, Expression, and Pharmacological Characterization of a Human $\alpha_{2B}$-Adrenergic Receptor," *Molecular Pharmacology 38*:681-688, 1990.

(List continued on next page.)

*Primary Examiner*—David Guzo
*Assistant Examiner*—Johnny F. Railey, II
*Attorney, Agent, or Firm*—Seed and Berry LLP

[57] ABSTRACT

Methods for treatment, processes for preparing, and compositions for delivering selected nucleic acid sequences to cells, primarily of the treatment of neurological disorders and exploring neurological functions, are disclosed. In particular, the invention provides recombinant Herpesvirus vectors with a high rate of expression of selected nucleic acid sequences and/or a low cytopathicity and its associated methods and processes.

13 Claims, 16 Drawing Sheets

OTHER PUBLICATIONS

Frielle et al., "Cloning of the cDNA for the human $\beta_1$–adrenergic receptor," *Proc. Natl. Acad. Sci. USA 84*: 7920–7924, 1987.

Dixon et al., "Cloning of the gene and cDNA for the mammalian β–adrenergic receptor and homology with rhodopsin," *Nature 321*:75–79, 1986.

Emorine et al., "Molecular Characterization of the Human $\beta_3$–Adenergic Receptor," *Science 245*: 1118–1121, 1989.

Gatzke et al., "Generation of Herpes Simplex Virus Recombinants for Altering Expression of Neurotransmitter Receptors in Infected Cells," *Society for Neuroscience Abstracts 19* (part 2):1339, abstract 551.7, 1993.

Meaney et al., "Development of Herpes Simplex Vectors for Virus–Mediated Gene Suppression in the CNS," *J. Cell. Biochem. Suppl. 17E*:202, abstract S 207, 1993.

Leib and Olivo, "Gene Delivery to Neurons: Is Herpes Simplex Virus the Right Tool for the Job?," *BioEssays 15*(8):547–554, 1993.

Johnson et al., "Cytotoxicity of a Replication–Defective Mutant of Herpes Simplex Virus Type 1," *Journal of Virology 66*(5):2952–2965, 1992.

Battleman et al., "HSV–1 Vector–Mediated Gene Transfer of the Human Nerve Growth Factor Receptor $p75^{hNGFR}$ Defines High–Affinity NGF Binding," *Journal of Neuroscience 13*(3):941–951, 1993.

Julius et al., "The 5HT2 receptor defines a family of structurally distinct but functionally conserved serotonin receptors," *Proc. Natl. Acad. Sci. USA 87*:928–932, 1990.

Glorioso et al., "Gene Transfer to Brain Using Herpes Simplex Virus Vectors," *Annals of Neurology 35*(Supp.):S28–S34, 1994.

Martin, J., "Gene therapy and pharmacological treatment of inherited neurological disorders," *Trends in Biotechnology 13*: 28–35, 1995.

Wood et al., "Inflammatory effects of gene transfer into the CNS with defective HSV–1 vectors," *Gene Therapy 1*(5):283–291, 1994.

Johnson et al., "Improved Cell Survival by the Reduction of Immediate–Early Gene Expression in Replication–Defective Mutants of Herpes Simplex Virus Type 1 but Not by Mutation of the Virion Host Shutoff Function," *Journal of Virology 68*(10):6347–6362, 1994.

RNAse Protection Assay To Detect M1 AchR Transcripts

Southern Blot of Viral DNA

METHOD OF USING, PROCESS OF PREPARING AND COMPOSITION COMPRISING RECOMBINANT HERPESVIRUS VECTORS

CROSS-REFERENCE TO RELATED APPLICATIONS

This application is a continuation-in-part of co-pending PCT application US94/12996, filed Nov. 10, 1994. PCT US94/12996 is a continuation of U.S. patent application Ser. No. 08/150,475, filed Nov. 10, 1993, now abandoned.

TECHNICAL FIELD

The subject invention is generally directed to a recombinant Herpesvirus vectors and more specifically, recombinant Herpesvirus vectors with a high rate of expression of foreign gene sequences and/or a low cytopathicity in neuronal cells.

BACKGROUND OF THE INVENTION

The capacity to introduce genetic sequences into a mammalian cell and to enable the expression of the gene is of substantial value in the fields of medical and biological research. This capacity allows a means for studying gene regulation, for defining the molecular basis for disease, and for designing a therapeutic basis for the treatment of disease.

The introduction of a genetic sequence into a mammalian host cell may be facilitated by first introducing the sequence into a suitable vector. However, vectors suitable for use in nonmitotic cells, such as neural or neuronal cells, has proven challenging. In addition, whereas most tissues in the body are readily accessible via the circulatory system, the brain is shielded by the blood-brain barrier and peripheral nerve cells may be encased in a myelin sheath. These physiological barriers, along with the non-replicative state of most nerve cells, present peculiar challenges when designing gene therapy systems.

These challenges have hindered the possible treatment of neurological disorders such as brain tumors, degenerative disorders (multiple sclerosis, Parkinson's disorder, Alzheimer's disease, amyotrophic lateral sclerosis), disorders caused by abnormal expression of genes, inherited disorders caused by a known gene defect (HPRT in Lesch-Nyhan disorder; retinblastoma (Lee et al., Sci. 235:1394, 1987); glucocerebrosidase (Sorge et al., *Proc. Natl. Acad. Sci. USA* 84:906, 1987); and Duchenne's muscular dystrophy (Monaco et al., Nature 321:443, 1986)) and acute injuries to the brain or peripheral nervous tissue, for example from a stroke, brain injury, or spinal cord injury.

Although many viral vector systems have been developed, there has been difficulty adapting these systems for neuronal cells. For example, although retroviral vectors have been used to transfer genes into neuronal cells in vitro (Price et al., *Proc. Natl. Acad. Sci USA* 34:156–160, 1987), and in vivo (Culver et al., *Science* 256:1550, 1992); Price et al., supra), they have not proven useful in delivering genes to a large proportion of cells in the nervous system. Other viral vector systems also have characteristics limiting their usefulness for gene transfer into neuronal cells, such as: rapidly clearing lytic infections (e.g., adenovirus, vaccinia virus), small genome size (SV40, polyoma), or limited cell tropism (EBV, bovine papilloma virus).

A Herpes Simplex Virus-1 (HSV-1) vector has been shown to be useful for infecting a wide variety of cells, including neuronal cells (Spear and Roizman, *DNA Tumor Viruses*, Cold Spring Harbor Laboratory, NY, pp. 615–746).

Briefly, HSV-1 can exist in a latent state in neural cells (Stevens, *Microbiol. Rev.* 53:318, 1989) allowing for maintenance of the vector. Additionally, the viral genome of HSV-1 is very large (150 kb) and may accommodate large nucleic acid segments.

Geller et al. (PCT WO 90/09441) developed a HSV-1 virus-based vector, which, while offering advantages over plasmid-based vectors, has failed to be efficacious in several instances. These vectors suffer from low gene expression and high cytopathicity, thus severely limiting their use in gene transfer. While others have tried to increase expression by using a variety of promoters (Tackney, et al, *J. Virol.* 52:606, 1984), cytopathicity has been shown to be a persistent problem, even in those viral vectors which are replication deficient (Johnson et al., *J. Virol.* 66:2952, 1992; Johnson et al., *Mol. Brain Res.* 12:95, 1992). For long-term expression in neuronal cells, it is necessary to have a viral vector that demonstrates low cytopathicity.

In view of the inability of current HSV-1 vectors to adequately account for the balance of cytopathicity and gene expression, it is apparent that there exists a need for new and additional methods and compositions which address and rectify the problem. The present invention fulfills this need, and further provides related advantages.

SUMMARY OF THE INVENTION

Briefly stated, the present invention provides expression cassettes capable of expressing a sequence of interest. Within one aspect such expression cassettes comprise one or more neuronal specific silencer elements, a promoter element operably linked to a sequence of interest, and an enhancer, wherein the enhancer and silencer elements are positioned such that they are not adjacent to one another.

Within one embodiment, the silencer element is a neuronal restrictive silencer element, and the promoter element is selected from the group consisting of CMV, SV40, herpes promoters and adenovirus promoters.

Within other aspects, expression cassettes are provided a LAT promoter operably linked to a sequence of interest, followed by an enhancer. Within further embodiments, such expression cassettes further comprise a neuronal-specific silencer element, wherein the enhancer and silencer elements are positioned on the vector such that they are not adjacent to one another. Within further embodiments, the expression cassettes are capable of expressing a sequence selected from the group consisting of antisense and ribozyme sequences, sequences which encode disease-associated antigens, sequences which encode immunologically active molecules, replacement genes, and toxic genes.

Within other aspects of the present invention, gene delivery construct, as well as host cells are provided which contain one of the above-identified expression cassettes. Representative examples of suitable host cells include cells from a warm-blooded animal or vertebrate, and includes in particular neuronal cells such as cortical neurons, cerebellar granule cells, retinal ganglia cells, hippocampal neurons, peripheral sensory neurons, and motor neurons.

Within another aspect of the present invention, methods are provided for producing a protein, comprising the steps of (a) introducing an expression cassette or gene delivery construct as described herein into a host cell, and (b) culturing the host cell under conditions, and for a time sufficient, to permit expression of the protein. Within further embodiments, such methods further comprise the step of purifying the protein.

Within other aspects of the present invention, methods are provided for introducing a selected sequence of interest into neuronal cells of a warm-blooded animal, comprising the step of administering to said animal an expression cassette or gene delivery construct provided herein. Such vectors may be administered by a variety of routes, including for example, subcutaneously, intracranially, intradermally, intramuscularly, intraperitoneally, or intravenously. Within other embodiments, the vector may be directly administered to a tumor.

Within other aspects, methods are provided for introducing a selected sequence of interest into an in vitro culture containing neuronal cells, comprising the step of introducing an expression cassette or gene delivery construct as described herein into an in vitro culture containing neuronal cells.

The present invention also provides recombinant Herpesvirus vectors capable of directing expression of a G protein linked receptor gene. Within certain embodiments of the invention, the recombinant viruses direct the expression of such genes in non-mitotic mammalian cells, and more preferably, in mammalian neuronal cells.

Within other aspects of the present invention, recombinant Herpesvirus vectors are provided which are capable of directing the expression of an antisense transcript of the G protein linked receptor gene.

In one embodiment of the invention, recombinant Herpesvirus vectors are provided which are deficient for the expression in one or more of the following: thymidine kinase; virion host shut-off protein (VHS); or a replication loci, such as that for ICP4 protein.

In another embodiment of the present invention, the gene encoding a G protein linked receptor or a antisense segment thereof is inserted in the TK locus of a Herpesvirus genome. For example, the antisense segment may be a 5-$HT_2$ receptor gene. Numerous G-protein linked receptor genes may be utilized within the context of the present invention, including, by way of example, a human M1 muscarinic acetylcholine receptor gene or an adrenergic receptor.

Within other aspects of the invention, methods of treating mammals for neurological disorders are provided, comprising the step of administering to a mammal a composition comprising an expression cassette or gene delivery construct such as a recombinant Herpesvirus vector, as described above. Within certain embodiments, this may be accomplished in combination with a pharmaceutically acceptable carrier or diluent.

Within certain embodiments, the administration of pharmaceutical compositions may be accomplished by, for example, by stereotactically microinjection, a time release mechanism, a sustained release mechanism, chronic infusion, or ex vivo mammalian cells infected with or containing a recombinant Herpesvirus vector, gene delivery constructs, or expression cassette according to the present invention.

Another aspect of the present invention provides pharmaceutical compositions comprising an expression cassette or gene delivery construct of the present invention and a pharmaceutically acceptable carrier or diluent.

Within yet other aspects of the present invention, processes of producing recombinant Herpesvirus vectors with low cytopathicity are provided, comprising the steps of culturing mammalian cells with a first recombinant Herpesvirus vector containing a G protein linked receptor gene and a second recombinant Herpesvirus vector defective in a gene required for replication under conditions and for a time sufficient to allow recombination of the first and second viruses; and, selecting the recombinant virus by detecting G protein linked receptor expression. Further, the G protein linked receptor gene can be inserted into the TK locus. Within certain embodiments, the first virus may be vhsA and the second virus may be d120.

Another aspect of the present invention is a process wherein the first recombinant virus is deficient in the expression of one or more of the following: the TK locus, the virion host shut-off protein (VHS), and the replication loci, such as that for ICP4 protein.

Other aspects of the present invention provide recombinant Herpesvirus vectors with an in vitro cytopathicity generally less than about 3%; typically in the range of 0.1% to 1.0%; and preferably in the range of about 0.001% to 0.1%.

Within yet other aspects, recombinant Herpesvirus vectors are provided which are capable of expressing a G protein linked receptor with a surface receptor expression generally of greater than about 10,000 receptors/cell; typically in the range of about 25,000–200,000 receptors/cell; preferably in the range of about 200,000 to about 400,000 receptors/cell; or more preferably, greater than about 400,000 receptors/cell.

Yet other aspects of the present invention provide methods of using an expression cassette or gene delivery construct (e.g., a recombinant Herpesvirus vector) in the manufacture of a medicament for the treatment of neuronal disorders.

These and other aspects of the present invention will become evident upon reference to the following detailed description and attached drawings. In addition, various references are set forth which describe in more detail certain procedures and/or compositions, and are hereby incorporated by reference in their entirety as if each were specifically incorporated by reference.

DETAILED DESCRIPTION OF THE INVENTION

Figure 1A:
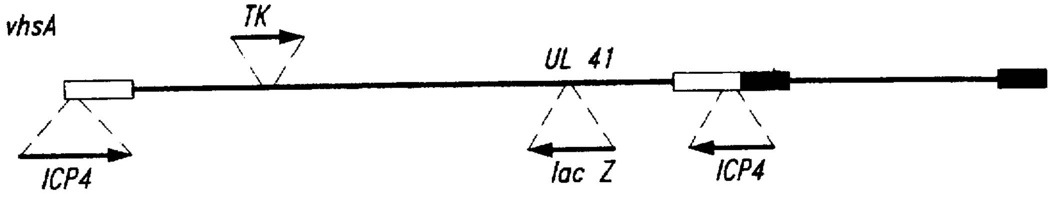
FIG. 1*a* is a schematic illustration of vhsA.

Prior to setting forth the invention, it may be helpful to an understanding thereof to first set forth definitions of certain terms that will be used hereinafter.

A "neuronal-specific silencer element" refers to a cis-acting sequence which down regulates or decreases the expression of a gene or sequence of interest in neuronal cells.

A "promoter element" refers to a sequence or sequences which facilitate the initiation of transcription.

An "enhancer" refers to a cis-acting sequence which functions to increase transcription of a promoter.

As noted above, the present invention provides expression cassettes which are suitable for a variety of in vivo and in vitro applications. As utilized herein, it should be understood that "expression cassettes" as utilized herein, refers to those vectors or molecules which are capable of directing the expression of a sequence of interest in neuronal cells. Within one embodiment, such cassettes generally comprise one or more neuronal specific silencer elements, a promoter element operably linked to a sequence of interest, and an enhancer, wherein the enhancer and silencer elements are positioned such that they are not adjacent or next to one another.

Use of such expression cassettes provides the surprising and unexpected advantage of substantially increased expression in neuronal cells (such as PC12), as compared to non-neuronal cells (such as Vero cells). Within certain embodiments the vectors provided herein provide greater than about 3-fold, about 5-fold, about 8-fold, or about 10-fold levels of expression in neuronal cells as compared to non-neuronal cells.

Such expression cassettes may be readily constructed given the disclosure provided herein, as well as standard recombinant techniques (see, e.g., Sambrook et al., "Molecular Cloning: A laboratory manual," 2nd ed., Cold Spring Harbor Laboratory Press, Cold Spring Harbor, N.Y.). Briefly, a wide variety of neuronal specific silencer elements may be utilized within the context of the present invention, including for example neural restrictive silencer elements "NRSE" (see Mori et al., Neuron 9(1):45–54, 1992; see also Schoenherr and Anderson, Science 267(5202):1360–1363, 1995, Devereux et al., *Nucleic Acids Res.* 12:387, 1984, and Altschul et al., *J. Mol. Biol.* 215:403, 1990, which describe related consensus sequences); silencer elements which are specific for cholinergic cells (e.g., Baskin et al., *Mol. Brain Res.* 30(1):106–114, 1995; Li et al., *J. Neurochem.* 61(2):748–751, 1993); silencer elements of the synapsin gene (Li et al., PNAS USA 90(4):1460–1464, 1993); silencer elements of the dopamine beta-hydroxylase gene (Ishiguro et al., *J. Biol. Chem.* 268(24):17984–17987, 1993); silencers of neuronal Na, K-ATPase subunit genes (Pathak et al., Nucleic Acids Res. 22:4748, 1994) and silencers of type II sodium channel genes (Kraner et al., Neuron 9:37–44, 1992).

The above-noted expression cassettes likewise contain promoter elements which facilitate the initiation of transcription. A wide variety of promoters may be utilized within the context of the present invention, including for example, both viral and cellular promoters. Representative examples of viral promoters include MoMLV LTR, RSV LTR, adenoviral promoter (Ohno et al., Science 265:781–784, 1994), late parvovirus promoter (Koering et al., *Hum. Gene Therap.* 5:457–463, 1994); Herpes promoters (see McGeoch et al., *J Gen. Virol.* 69:1531–1574, 1988 and Ward and Roizman, *Trends in Gen.* 10(8):267–274, 1994) such as the TK promoter, ICP6 promoter, ICP4 promoter, VP16 promoter or latency-associated promoters (e.g., HSV-1 LAT promoter (Ho and Mocarski, *Proc. Natl Acad. Sci. USA* 86:7596–7600, 1989)); SV40 promoters (Subramani et al., *Mol. Cell. Biol.* 1:854–864, 1981), cytomegalovirus immediate early promoter (Boshart et al., Cell 41:521–530, 1985), and the cytomegalovirus immediate late promoter. Representative examples of cellular promoters include the neomycin phosphotransferase promoter; metallothionein-1 promoter (Palmiter et al., U.S. Pat. No. 4,579,821, and the mouse VH promoter (Loh et al., Cell 33:85–93, 1983). Other suitable promoters include tissue or cell-specific promoters (see e.g., WO 91/02805; EP 0,415,731; and WO 90/07936). Representative examples of suitable neuron specific promoters include tα1 tubulin (Gloster et al., *J. Neurosci.* 14(12):7319–30, 1994), and the neuronal nicotinic acetylcholine receptor alpha 2 subunit gene promoter (Milton et al., *J. Biol. Chem.* 270(25):15143–7, 1995).

The above-noted expression cassettes may also contain enhancer elements, which are cis-acting sequences which function to upregulate transcription from a nearby promoter. Representative examples include the CMV enhancer, the SV40 enhancer, and the 5' enhancer of the MMTV LTR (Mellentin-Michelotti et al., *J. Biol. Chem.* 269(50):31983–90, 1994)

The above-noted expression cassettes may be readily constructed in order to allow substantially increased levels of expression in neuronal cells. For example, within one embodiment expression cassettes are constructed with the following ordered elements (in a 5' to 3' orientation): the LAP1 promoter operably linked to a sequence of interest, followed by the hCMV enhancer. Within other embodiments, expression cassettes are provided with the following ordered elements: one or more neuronal restrictive silencer elements, a LAP1 promoter operably linked to a sequence of interest, and an hCMV enhancer. Within certain preferred embodiments, the neuronal restrictive silencer elements may be in the same transcriptional orientation as the LAP1 promoter, or alternatively, in an opposite and divergent transcriptional orientation.

Such expression cassettes may be utilized in a variety of constructs and methods, as described in more detail below. For example, such expression cassettes may be delivered directly to an in vitro cell culture or to a warm-blooded animal by a variety of techniques, including for example by itself (WO 90/11092), in liposomes, condensed with polycations linked or unlinked to killed adenovirus (Curiel et al., *Hum. Gene Ther.* 3:147–154, 1992), or linked to a ligand (Wu et al., *J. Biol. Chem* 264:16985–16987, 1989).

GENE DELIVERY CONSTRUCTS

In addition to expression cassettes, which are useful by themselves for transfecting cells or therapeutic purposes, the present invention also provides gene delivery constructs which are useful for carrying and/or delivering the above-described expression cassettes. Representative examples of such constructs include a variety of non-viral and viral vectors, as described below, as well as cells which are capable of producing such vectors.

For example, within one aspect of the invention retroviral vectors may be utilized as gene delivery constructs suitable for delivering the above-noted expression constructs. Representative examples of such retroviral vectors include those described within EP 0,415,731, WO 90/07936, WO 91/0285, WO 94/03622, WO 93/25698, WO 93/25234, U.S. Pat. No. 5,219,740, WO 93/11230, WO 93/10218, U.S. Pat. No. 4,777,127, EP 0,345,242 and WO 91/02805).

Other examples of suitable gene delivery constructs may be found in the Herpesvirus family. Briefly, suitable members of the Herpesviridae include both primate Herpesviruses, and nonprimate Herpesviruses such as avian Herpesviruses. Representative examples of suitable Herpesviruses include Herpes Simplex Virus Type 1 (McKnight et al., *Nuc. Acids Res.* 8:5949–5964, 1980; Fields et al., *Fundamental Virology*, Raven Press, N.Y. (1986)), Herpes Simplex Virus Type 2 (Swain and Galloway, *J. Virol.* 46:1045–1050, 1983), Varicella Zoster Virus (Davison and Scott, *J. Gen. Virol.* 67:1759–1816, 1986) and Epstein-Barr virus (Baer et al., *Nature (London)* 310:207–311, 1984). Particularly preferred Herpesvirus vectors include those described below, which are deficient in the expression of one or more of: the virion host shut-off protein VHS; a replication loci such as ICP4; or thymidine kinase. Representative examples of such vectors include vTKhm1-1, vTKhm1-2 and vTKhm1-3.

Herpesviruses may be readily obtained from commercial sources such as the American Type Culture Collection ("ATCC", Rockville, Maryland). Deposits of certain of the above-identified Herpesviruses may be readily obtained from the ATCC, for example: ATCC No. VR-539 (Herpes simplex type 1); ATCC Nos. VR-734 and VR-540 (Herpes Simplex type 2); and ATCC No. VR-586 (Varicella Zoster Virus). Herpesviruses may also be readily isolated and identified from naturally occurring sources (e.g., from an infected animal).

In addition to retroviral vectors and Herpes viral vectors, a wide variety of other gene delivery constructs may be utilized to deliver expression cassettes, including for example constructs derived from adenovirus (Rosenfeld et al., *Science* 252:431–434, 1991; Kolls et al., *PNAS* 91(1):215–219, 1994; Kass-Eisler et al., *PNAS* 90(24):11498–502, 1993; Levrero et al., Gene 101(2):195–202, 1991); and Guzman et al., *Circulation* 88(6):2838–48, 1993; alphaviruses such as Semliki Forest Virus and Sindbis Virus (Xiong et al., *Science* 243:1188, 1989; Raju and Huang, *J. Vir.* 65(5):2501–2510, 1991; Hertz and Huang, *J. Vir.* 66(2):857–864, 1992, WO 92/10578; WO 95/07994; U.S. Pat. No. 5,091,309); influenza virus (Luytjes et al., Cell 59:1107–1113, 1989; McMicheal et al., *N. Eng. J. Med.* 309:13–17, 1983; and Yap et al., Nature 273:238–239, 1978); pox viruses, such as canary pox virus or vaccinia virus (Fisher-Hoch et al., PNAS 86:317–321, 1989; Flexner et al., *Ann. NY. Acad. Sci.* 569:86–103, 1989; U.S. Pat. Nos. 4,603,112, 4,769,330 and 5,017,487; WO 89/01973); SV40 (Mulligan et al., Nature 277:108–114, 1979); parvovirus such as adeno-associated virus (Samulski et al., *J. Vir.* 63:3822–3828, 1989; Plotte et al., *G. Biol. Chem.* 268:3781–3790, 1993; Flotte et al., PNAS 90(22):10613–10617, 1993 WO95/13365); and HIV (Poznansky, *J. Virol.* 65:532–536, 1991).

Other non viral vector systems that may also be utilized include a variety of nucleic acid based transcription systems (e.g., based on T7 or SP6 promoters, see generally, WO 95/07994). Such vector systems may be administered and prepared as described above (e.g., in liposomes, condensed with polycations, or linked to a ligand).

SEQUENCES OF INTEREST

A wide variety of heterologous nucleic acid sequences (also referred to as nucleic acid segments or molecules) may be expressed by the expression cassettes and gene delivery constructs of the present invention, including for example, antisense, ribozyme or regulatory sequences, as well as a wide variety of proteins such as immunogenic portions of disease-associated antigens, immunologically active molecules, replacement genes and toxic genes.

Representative examples of antisense and ribozyme sequences include those sequences which inhibit, for example, tumor cell growth, viral replication, or a genetic disease by preventing the cellular synthesis of critical proteins. Examples of such antisense sequences include antisense ABL (Fainstein et al., *Oncogene* 4:1477–1481, 1989), antisense HER2 (Coussens et al., Science 230:1132–1139, 1985), antisense *myc* (Stanton et al., *Nature* 310:423–425, 1984), antisense ras and antisense CPP32 or ice proteases.

Representative examples of ribozyme sequences include hammerhead ribozymes (for example, as described by Forster and Symons, *Cell* 48:211–220, 1987; Haseloff and Gerlach, *Nature* 328:596–600, 1988; Walbot and Bruening, *Nature* 334:196, 1988; Haseloff and Gerlach, *Nature* 334:585, 1988) and hairpin ribozymes (for example, as described by Haseloff et al., U.S. Pat. No. 5,254,678 and Hempel et al., European Patent Publication No. 0 360 257) which have the ability to specifically target, cleave and inactivate RNA or MRNA. Briefly, the sequence requirement for the hairpin ribozyme is any RNA sequence consisting of NNNBN*GUCNNNNNNNN (where N*G is the cleavage site, wherein B is any of G, C, or U, and where N is any of G, U, C, or A) (Sequence I.D. No. 1). The sequence requirement at the cleavage site for the hammerhead ribozyme is any RNA sequence consisting of NUX (where N is any of G, U, C, or A and X represents C, U or A) can be targeted. Accordingly, the same target within the hairpin leader sequence, GUC, is useful for the hammerhead ribozyme. The additional nucleotides of the hammerhead ribozyme or hairpin ribozyme is determined by the target flanking nucleotides and the hammerhead consensus sequence (see Ruffner et al., *Biochemistry* 29:10695–10702, 1990).

"Disease-associated" antigens should also be understood to include all, or various portions (e.g., immunogenic portions) of eukaryotic (including for example, parasites), prokaryotic (e.g., bacterial) or viral pathogens. Other "disease-associated" antigens include tumor-associated antigens such as ras, p53 and CEA.

Immunologically active molecules may also be expressed by the expression cassettes and gene delivery constructs described herein. As utilized within the context of the present invention, it should be understood that "immunologically active molecules" refers to those molecules which can either increase or decrease the recognition, presentation or activation of a cell-mediated or humoral immune response. Representative examples of immunologically active molecules include lymphokines such as IL-1, IL-2, IL-3, IL-4, IL-5, IL-6, IL-7, IL-8, IL-9, IL-10, IL-11, IL-12 (WO 90/05147; EPO 433,827), IL-13 (WO 94/04680), IL-14, IL-15, α, β, or γ-interferon, GM-CSF, M-CSF-1, G-CSF, ICAM-1 (Simmons et al., *Nature* 331:624–627, 1988), ICAM-2 (Singer, Science 255:1671, 1992), β-microglobulin (Parnes et al., *PNAS* 78:2253–2257, 1981), HLA Class I, HLA Class II molecules, B7 (Freeman et al., *J. Immun.* 143:2714, 1989), and B7-2, as well as their respective receptors. Other biologically active molecules that may likewise be utilized in the context of the present invention include neurotrophins such as nerve growth factor (NGF), brain derived growth neurotrophic factor (BDGF), glial-derived neurotrophic factor (GDNF), neurotrophin-3 (NT-3), tumor necrosis factor (TNF) as well as their respective receptors.

Within certain aspects of the present invention, the expression cassettes and gene delivery constructs described herein may direct the expression of more than one heterologous sequence. Such multiple sequences may be controlled either by a single promoter, or alternatively, by additional secondary promoters (e.g., Internal Ribosome Entry Sites or "IRES"). Within further embodiments of the invention, expression cassettes or gene delivery constructs are provided which direct the expression of heterologous sequences which act synergistically (e.g., a disease-associated antigen, and an immunologically active molecule, such as IL-2, IL-12 or γ-interferon).

Within other aspects of the invention, the expression cassettes or gene delivery constructs described herein may direct the expression of one or more heterologous sequences which encode "replacement" genes. As utilized within the context of the present invention, the term "replacement genes" refers to a nucleic acid molecule which encodes a therapeutic protein that is capable of preventing, inhibiting, stabilizing or reversing an inherited or noninherited genetic defect. Representative examples of such genetic defects include disorders in metabolism, immune regulation, hormonal regulation, and enzymatic or membrane associated structural function. Specific examples include Alzheimer's Disease (see, for example, Goat et al., *Nature* 349:704, 1991; Sherrington et al., Nature 375:754, 1995; Levy-Labad et al., *Science* 269:973, 1995) and Huntington's Disease (see EP 0 614,977 and WO 94/21790). Replacement genes may also be administered for specific conditions, such as the administration of anti-apoptotic genes or sequences such as Bcl-2, BclX or Bax (Oitvai et al., Cell 74:609–619, 1993), neuronal apoptosis inhibitory protein ("NAIP", Roy et al., Cell 80:1–20, 1995), or TNF (Zheng et al., *Nature* 377:348–351, 1995) in order to inhibit or remedy conditions or disease where apoptosis occurs.

Representative examples of toxic genes which may be expressed and/or delivered by the expression cassettes and gene delivery constructs provided herein include genes which encode proteins such as abrin (Wood et al., *Eur. J. Biochem.* 198:723–732, 1991), diphtheria toxin (Tweten et al., *J. Biol. Chem.* 260:10392–10394, 1985), antiviral protein (Barbieri et al., *Biochem. J.* 203:55–59, 1982; Irvin et al., *Arch. Biochem. & Biophys.* 200:418–425, 1980), cholera toxin (Mekalanos et al., *Nature* 306:551–557, 1983; Sanchez and Holmgren, *PNAS* 86:481–485, 1989), gelonin (Stirpe et al., *J. Biol. Chem.* 255:6947–6953, 1980), pokeweed (Irvin, *Pharmac. Ther.* 21:371–387, 1983), ricin (Lamb et al., *Eur. J. Biochem.* 148:265–270, 1985), Shigella toxin (Calderwood et al., *PNAS* 84:4364–4368, 1987), tritin, and Pseudomonas exotoxin A (Carroll and Collier, *J. Biol. Chem.* 262:8707–8711, 1987).

Within other aspects of the invention, heterologous sequences should be understood to include gene products which activate a non-toxic product into a toxic product. Representative examples of such gene products include thymidine kinases which activate a nucleoside analogue such as acyclovir or gancyclovir, as well as other "prodrugs"

(see WO 93/10218; WO 93/01281; WO 93/08843; WO 93/08844; and WO 90/07936 ).

As should be evident from the above discussion, expression cassettes of the present invention may be utilized to express a wide variety of additional sequences, including for example those encoding receptors (including, for example, G protein linked receptors as described in more detail below), regulatory proteins, enzymes and structural proteins not specifically set forth above.

Sequences which encode the above-described heterologous genes may be readily obtained from a variety of sources. For example, plasmids which contain sequences that encode immunologically active molecules may be obtained from a depository such as the American Type Culture Collection (ATCC, Rockville, Md.), or from commercial sources such as British Bio-Technology Limited (Cowley, Oxford, England). Representative sources sequences which encode the above-noted immune accessory molecules include ATCC No. 20663 (which contains sequences encoding alpha interferon), ATCC Nos. 31902 and 39517 (which contains sequences encoding beta interferon), ATCC Nos. 39405, 39452, 39516, 39626 and 39673 (which contains sequences encoding Interleukin-2), ATCC Nos. 59399, 59398, and 67326 (which contain sequences encoding Interleukin-3), ATCC No. 57592 (which contains sequences encoding Interleukin-4), ATCC Nos. 59394 and 59395 (which contain sequences encoding Interleukin-5), and ATCC No. 67153 (which contains sequences encoding Interleukin-6). It will be evident to one of skill in the art that one may utilize either the entire sequence of the protein, or an appropriate portion thereof which encodes the biologically active portion of the protein.

Alternatively, known cDNA sequences which encode cytotoxic genes or other heterologous genes may be obtained from cells which express or contain such sequences. Briefly, within one embodiment mRNA from a cell which expresses the gene of interest is reverse transcribed with reverse transcriptase using oligo dT or random primers. The single stranded cDNA may then be amplified by PCR (see U.S. Pat. Nos. 4,683,202, 4,683,195 and 4,800,159. See also PCR Technology: Principles and Applications for DNA Amplification, Erlich (ed.), Stockton Press, 1989 all of which are incorporated by reference herein in their entirety) utilizing oligonucleotide primers complementary to sequences on either side of desired sequences. In particular, a double stranded DNA is denatured by heating in the presence of heat stable Taq polymerase, sequence specific DNA primers, ATP, CTP, GTP and TTP. Double-stranded DNA is produced when synthesis is complete. This cycle may be repeated many times, resulting in a factorial amplification of the desired DNA.

Sequences which encode the above-described genes may also be synthesized, for example, on an Applied Biosystems Inc. DNA synthesizer (e.g., ABI DNA synthesizer model 392 (Foster City, Calif.)).

G PROTEIN-LINKED RECEPTORS, AND RECOMBINANT HERPESVIRUS VECTORS

Within the various aspects of the present invention, the expression cassettes or gene delivery vehicles described herein (e.g., recombinant Herpesvirus vectors may be utilized as a means of introducing nucleic acid segments into nonmitotic cells primarily of the nervous system (collectively referred to as "neural" or "neuronal" cells). For example, recombinant Herpesvirus vectors of the present invention may be utilized to deliver nucleic acid segments into the cell where the proteins are expressed, generally as MRNA which is then translated into a protein. When the protein translated is a G protein linked receptor, for example, the protein enters the secretory pathway of the host cell and is expressed on the cell surface as a receptor. The receptors are in the correct orientation to bind their associated ligand and linked to a second messenger system and, thus, function in much the same manner as a naturally occurring receptor.

Briefly, Herpesviruses such as HSV-1 are double stranded DNA viruses (approx. 152 kb) which are replicated and transcribed in the nucleus of the cell. Although HSV-1 is utilized as a representative Herpesvirus in the description and examples provided below, it should be understood that the present invention is not so limited. In particular, numerous other Herpesviruses (including for example, those described above), may be utilized within the context of the present invention.

Productive infection by HSV-1 usually results in cell lysis or alteration of host macromolecular processes. However, HSV-1 also may be maintained indefinitely in the "latent state" in certain cells by a mechanism involving the tegument of the virus particles. The reactivation of the virus is regulated by certain systemic or cellular events. The latent virus is still transcriptionally active, producing "latency associated transcripts" (LATS). Mutant viruses that are compromised or defective in their replication potential can still enter the latent state (e.g., UL41(−), TK(−), and ICP4 (−)). In fact, a TK(−) HSV-1 will maintain the latent state indefinitely. Thus, HSV-1 is ideal for use in delivering nucleic acid segments to non-mitotic cells such as neuronal cells. Within the present invention, Herpesvirus vectors such as those derived from HSV-1 are preferably maintained in the latent state.

The manipulation of Herpesviruses such as HSV-1 for the purposes of the present invention, may, within certain aspects involve deletions, substitutions or mutations of nonessential regions of a Herpesvirus genome, generally maintaining the essential regions intact. In the context of the present invention, "essential region" refers to any region of the viral genome the deletion of which would result in an inability to infect a mammalian host cell or an inability to replicate, even with the assistance of a helper virus or a complementing cell line. Nonessential regions within the genome may, but need not be, deleted in whole or in part.

Within the context of the present invention, the term "helper viruses" refers to replication competent infectious viruses that provide gene products required for the propagation of replication defective viruses that can not, by definition, propagate themselves. Such helper viruses are described in Fields et al., *Fundamental Virology,* Raven Press, N.Y. (1986), and are well known to those skilled in the art. Examples of helper viruses suitable for use in the present invention include unaltered Herpesviruses such as HSV-1 as well as other viruses that express the genes contained within the deleted region whose products are necessary for propagation of a recombinant Herpesvirus.

The term "complementing cell lines" refers to cell lines that provide gene products required for the propagation of defective viruses that by definition cannot propagate themselves. Suitable complementing cell lines in the present invention include E5 Vero cells, which provide the protein ICP4 for replication deficient viruses. (Disclosed in detail in DeLuca et al., *J. Vir.* 56:558–570, 1985.)

As noted above, within certain aspects of the present invention, nucleic acid segments are inserted into a Herpesvirus genome and/or portions of the Herpesvirus genome are deleted. Preferably, insertions or deletions of nucleic acid segments utilized in the present invention are made to one or more of the following nonessential regions: the UL41, thymidine kinase (TK), and/or any one of several replication loci (Ward and Roizman, *Trends in Gen.* 10:267, 1994). The replication loci include DNA polymerase and that for the ICP4 protein. Briefly, ICP4 is a protein produced by a viral immediate-early gene and governs transcriptional regulators required for the expression of the early genes. Likewise, Thymidine kinase is an early gene implicated in the replication of viral DNA. UL41 is a late gene whose protein product is responsible for early shut off of host cell macromolecular synthesis.

The Herpesvirus genome can be manipulated to produce such deletions and insertions by using standard recombinant DNA techniques, such as those described in Maniatis et al., *Molecular Cloning, A Laboratory Manual*, Cold Spring Harbor Laboratory, Cold Spring Harbor, N.Y. (1982), or Sambrook et al., *Molecular Cloning, A Laboratory Manual*, 2nd Ed., Cold Spring Harbor Laboratory Press, Cold Spring Harbor, N.Y. (1989). Briefly, deletions within a Herpesvirus genome can be effected by conventional techniques employing endonucleases, exonucleases and the like. Insertions can also be executed using conventional techniques, including, by way of example cotransfection, ie., homologous recombination facilitated by a suitable plasmid. A suitable plasmid available for such use includes pRc/CMV (Invitrogen Corp.). The plasmid including the desired characteristics can be selected using conventional methods and introduced for propagation purposes into a host cell or organism using standard transformation procedures. The plasmid is then isolated from the host organism, mixed with unaltered Herpesvirus DNA and cotransfected into host cells. The cells containing the plasmid and the Herpesvirus DNA are cultured, and homologous recombination take place, resulting in the replacement of the unaltered region in the viral DNA with the corresponding altered region from the plasmid. Any host cell suitable for plasmid and Herpesvirus DNA transfection and subsequent recombinant virus propagation can be utilized in this procedure. The recombinant Herpesvirus DNA is then replicated within the cell and the viruses which have undergone the desired recombination are selected using standard techniques.

As noted above, recombinant Herpesvirus of the present invention are produced through insertion of nucleic acid segments into the genome. Within the context of the present invention, "nucleic acid segment" refers to a nucleic acid sequence or molecule, and may be derived from a variety of sources including DNA, cDNA, synthetic DNA, RNA, or combinations thereof. Such nucleic acid segments may comprise genomic DNA which may or may not include naturally occurring introns. Such genomic DNA may be obtained in association with promoter regions or poly A sequences. Further, The nucleic acid segment may be an antisense sequence. The nucleic acid segments of the present invention are preferably cDNA. Genomic DNA or cDNA may be obtained in any of several ways. Genomic DNA can be extracted and purified from suitable cells by any one of several means. Alternatively, niRNA can be isolated from a cell and used to produce cDNA by reverse transcriptase by any one of several methods.

Within particular preferred embodiments of the present invention, the nucleic acid segment is a G protein linked receptor gene. In the context of the present invention, the term "G protein linked receptor" refers to a guanine nucleotide binding regulatory protein coupled to both a cell surface receptor and an effector, such as an ion channel, together comprising a transmembrane signaling system. G protein linked receptors mediate the actions of extracellular signals, such as neurotransmitters. They are described in detail in Dohlman et al., *Ann. Rev. Biochem.* 60:553–588 (1991). Suitable G protein linked receptors genes include those listed in Table I and portions thereof.

It will be evident to those skilled in the art that the particular receptor utilized will be influenced by the characteristics of the receptor and the specific treatment.

TABLE 1

| Receptor Subtype | Species | Ref. |
|---|---|---|
| Mammalian | | |
| $\beta_1$-adrenergic | Human | Frielle, T., et al., Proc. Natl. Acad. Sci. USA 84:7920–24, 1987. |
| | Rat | Machida, C. A., et al., J. Biol. Chem. 265:12960–65, 1990. |
| $\beta_2$-adrenergic | Hamster | Dixon, R. A. F., et al., Nature 321:75–79, 1986. |
| | Human | Kobilka, B. K., et al., Proc. Natl. Acad. Sci. USA 84:46–50, 1987. |
| | | Schofield, P. R., et al., Nucleic Acids Res. 15:3636, 1987. |
| | | Chung, F. Z., et al., FEBS Lett 211:200–6, 1987. |
| | | Emorine, L. J., et al., Proc. Natl. Acad Sci. USA 84: 6995–99, 1987. |
| | Mouse | Allen, J. M., et al., EMBO J. 7:133–38, 1988. |
| | Rat | Gocayne, J., et al., Proc. Natl. Acad. Sci. USA 84:8296–300, 1987. |
| | | Buckland, P. R., et al., Nucleic Acids Res. 18:682, 1990. |
| $\beta_3$-adrenergic | Human | Emorine, L. J., et al., Science 245:1118–21, 1989. |
| $\alpha_{1B}$-adrenergic | Hamster | Cotecchia, S., et al., Proc. Natl. Acad. Sci. USA 85:7159:63, 1988. |
| | Rat | Voigt, M. M.,, et al., Nucleic Acids Res. 18:1053, 1990. |
| $\alpha_{1C}$-adrenergic | Cow | Schwinn, D. A., et al., J. Biol. Chem. 265:8183–89, 1990. |
| $\alpha_{2A}$-adrenergic | Human | Kobilka, B. K., et al., Science 238:650–56, 1987. |
| | | Fraser, C. M. et al., J. Biol. Chem. 264:11754–61, |

TABLE 1-continued

| Receptor Subtype | Species | Ref. |
|---|---|---|
| | | 1989. |
| | Rat | Chalberg, S. C., et al., Mol. Cell. Biochem. 97:161–72, 1990. |
| | Pig | Guyer, C. A., et al., J. Biol. Chem., 265:17307–17, 1990. |
| $\alpha_{2B}$-adrenergic | Human | Regan, J. W. et al., Proc. Nat'l. Acad. Sci. USA 85:6301–5, 1988. |
| | Rat | Zeng, D. W. et al., Proc. Nat'l. Acad Sci. USA 87:3102–6, 1990. |
| $\alpha_{2C}$-adrenergic | Human | Lomasney, J. W. et al., Proc. Nat'l. Acad. Sci. USA 87:5094–98, 1990. |
| 5-HT1a-serotonergic | Human | Kobilka, B. K., et al., Nature 329:75–79, 1987. Fargin, A., et al., Nature 335:358–60, 1988. |
| | Rat | Albert, P. R., et al., J. Biol. Chem. 265:5825–32, 1990. |
| 5-HT1c-serotonergic | Rat | Julius, D., et al., Science 241:558–64, 1988. |
| 5-HT2-serotonergic | Rat | Pritchett, D. B., et al., EMBO J. 7:4135–40, 1988. Julius, D. et al., Proc. Nat'l. Acad. Sci. USA 87:928–32, 1990. |
| M1-muscarinic | Pig | Kubo, T., et al., Nature 323:411–16, 1986. |
| | Human | Peralta, E. G., et al., EMBO J. 6:3923–29, 1987. Allard, W. J., et al., Nucleic Acids Res. 15:10604, 1987. |
| | Rat | Bonner, T. I., et al., Science 237:527–32, 1987. |
| | Mouse | Shapiro, R. A., et al., J. Biol. Chem. 263:18397–403, 1988. |
| M2-muscarinic | Pig | Kubo, T., et al., FEBS Lett. 209:367–72, 1986. Peralta, E. G., et al., Science 236:600–5, 1987. |
| | Human | Peralta, E. G., et al., EMBO J. 6:3923–29, 1987. |
| | Rat | Gocayne, J., et al., Proc. Nat'l. Acad Sci USA 84:8296–300, 1987. Bonner, T. I., et al., Science 237:527–32, 1987. |
| M3-muscarinic | Human | Peralta, E. G., et al., EMBO J. 6:3923–29, 1987. |
| | Rat | Bonner, T. I., et al., Science 237:527–32, 1987. |
| M4-muscarinic | Human | Peralta, E. G., et al., EMBO J. 6:3923–29, 1987. |
| | Rat | Braun, T., et al., Biochem. Biophys. Res. Commun. 149:125–32, 1987. |
| | Pig | Akiba, I., et al., FEBS Lett. 235:257–61, 1988. |
| M5-muscarinic | Human | Bonner, T. I., Neuron, 1:403–10, 1988. |
| | Rat | Bonner, T. I., Neuron, 1:403–10, 1988. Liao, C. F., et al., J. Biol. Chem. 264:7328–37, 1989. |
| $D_1$-dopaminergic | Human | Dearry, A., et al., Nature 347:72–75, 1990. Zhou, Q. Y., et al., Nature 347:76–80, 1990. |
| | Rat | Zhou, Q. Y., et al., Nature 347:76–80, 1990. O'Dowd, B. F., et al., FEBS Lett. 347:8–12, 1990. |
| $D_2$-dopaminergic | Rat | O'Dowd, B. F., et al., FEBS Lett. 347:8–12, 1990. Todd, R. D., et al., Proc. Nat'l. Acad. Sci. USA 86:10134–38, 1989. |
| | Human | Todd, R. D., et al., Proc. Nat'l. Acad. Sci. USA 86:10134–38, 1989. Grandy, D. K., et al., Proc. Nat'l. Acad Sci USA 86:9762–66, 1989. |
| | alternatively spliced | Monsma, F. J., Jr., et al., Nature 342:926–29, 1989. Miller, J. C., Biochem. Biophys. Res. Commun. 166:109–12, 1990. |
| $D_3$-dopaminergic | Rat | Sokoloff, P., et al., Nature 347:146–51, 1990. |
| Substance K | Cow | Masu, Y., et al., Nature 329:836–38, 1987. |
| | Rat | Sasai, Y., et al., Biochem. Biophys. Res. Commun. 165:695–702, 1989. |
| | Human | Gerard, N. P., et al., J. Biol. Chem. 265:20455–62, 1990. |
| Neuromedin K | Rat | Shigemoto, R., et al., J. Biol. Chem. 265:623–28, 1990. |
| Substance P | Rat | Yokota, Y., et al., J. Biol. Chem. 264:17649–52, 1989. Hershey, A. D., et al., Science 247:958–62, 1990. |
| F—Met—Leu—Phe | Human | Thomas, K. M., et al., J. Biol. Chem. 265:20061–64, 1990. |
| Thyrotropin | Dog | Parmentier, M., et al., Science 246:1620–22, 1989. Libert, F., et al., Mol. Cell. Endocrinol. 68:R15–17, 1990. |
| | Human | Libert, F., et al., Biochem. Biophys. Res. Commun. 165:1250–55, 1989. Nagayama, Y., et al., Biochenm. Biophys. Res. Commun. 165:11845–90. |
| | Rat | Akamizu, T., et al., Proc. Nat'l. Acad. Sci. USA |

TABLE 1-continued

| Receptor Subtype | Species | Ref. |
|---|---|---|
| | | 87:5677-81, 1990. |
| Lutropin-choriogonadotropin | Rat | McFarland, K. C., et al., Science 245:494-99, 1989. |
| | Pig | Loosfelt, H., et al., Science 245:525-28, 1989. |
| Endothelin | Human | Minegiah, T., et al., Biochem. Biophys. Res. Commun. 172:1049-54, 1990. |
| | Cow | Arai, H., et al., Nature 348:730-32, 1990. |
| Endothelin-$ET_B$ | Rat | Sakurai, T., et al., Nature 348:732-35, 1990. |
| Angiotensin (mas) | Human | Young, D., et al., Cell 45:711-19, 1986. |
| | | Jackson, T. R., et al., Nature 335:437-40, 1988. |
| | Rat | Young, D., et al., Proc. Nat'l. Acad. Sci. USA 85:5339-42, 1988. |
| Rhodopsin | Cow | Hargrave, P. A., Prog. Retinal Res. 1:1-51, 1982. |
| | | Ovchinnikov, Y. A., FEBS Lett. 148:179-91, 1982. |
| | | Nathans, J., et al., Cell 34:807-14, 1983. |
| | Human | Nathans, J., et al., Proc. Nat'l. Acad. Sci. USA 81:4851-55, 1984. |
| | Mouse | Baehr, W., et al., FEBS Lett. 238:253-56, 1988. |
| Red opsin | Human | Nathans, J., et al., Science 232:193-202, 1986. |
| Green opsin | Human | Nathans, J., et al., Science 232:193-202, 1986. |
| Blue opsin | Human | Nathans, J., et al., Science 232:193-202, 1986. |
| Cannabinoid | Rat | Matsuda, L. A., et al., Nature 346:561-64, 1990. |
| Unknown-RDC1 | Dog | Libert, F., et al., Science 244:569-72, 1991. |
| Unknown-RDC4 | Dog | Libert, F., et al., Science 244:569-72, 1991. |
| Unknown-RDC7 | Dog | Libert, F., et al., Science 244:569-72, 1991. |
| Unknown-RDC8 | Dog | Libert, F., et al., Science 244:569-72, 1991. |
| Unknown-edg1 | Human | Hla, T., et al., J. Bio. Chem. 265:9308-13, 1990. |
| Unknown-RTA | Rat | Ross, P. C., et al., Proc. Nat'l. Acad. Sci. USA 87:3052-56, 1990. |
| Nonmammalian | | |
| Adrenergic ($\beta_1$-) | Turkey | Yarden, Y., et al., Proc. Nat'l. Acad. Sci. USA 83:6795-99, 1986. |
| Serotonergic | Fly | Witz, P., et al., Proc. Nat'l. Acad. Sci. USA 87:8940-44, 1990. |
| Muscarinic | Chicken | Tietje, K. M., et al., J. Biol. Chem. 2_-2828-34, 1990. |
| | Fly | Shapiro, R. A., et al., Proc. Nat'l. Acad. Sci. USA 86:9039. |
| | | Onai, T., et al., FEBS Lett. 255:219-25, 1989. |
| Opsin (ninaE) | Fly | O'Tousa, J. E., et al., Cell 40:839-50, 1985. |
| | | Zuker, C. S., Cell 40:851-58, 1985. |
| Opsin-Rh2 | Fly | Cowman, A. F., Cell 44:705-10, 1986. |
| Opsin-Rh3 | Fly | Zuker, C. S., et al., Neurosci. 7:1550-57, 1987. |
| Opsin-Rh4 | Fly | Fryxell, K. J., et al., EMBO J. 6:443-51, 198_. |
| | | Montell, C., et al., J. Neurosci. 7:1558-_. |
| Rhodopsin | Fly | Ovchinnikov, Yu. A., et al., FEBS Lett. 232:69-72, 1988. |
| | Chicken | Takao, M., et al., Vision Res. 28:471-80, 1988. |
| Octopamine | Fly | Arakawa, S., et al., Neuron 4:343-54, 1990. |
| Mating factor | | |
| (STE2) | Yeast | Marsh, L., et al., Proc. Nat'l. Acad. Sci. USA 87:3855-59, 1988. |
| | | Burkholder, A. C., et al., Nucleic Acids Res. 13:8463-75, 1985. |
| | | Nakayama, N., et al., EMBO J. 4:2643-48, 1985. |
| (STE3) | Yeast | Nakayama, N., et al., EMBO J. 4:2643-48, 1985. |
| | | Hagen, D. C., et al., Proc. Nat'l. Acad. Sci. USA 83:1418-22, 1986. |
| cAMP | Slime mold | Klein, P. S., et al., Science 241:146-72, 1988. |
| Unknown-US27 | Viral | Chee, M. S., et al., Nature 344:774-77, 1990. |
| Unknown-US28 | Viral | Chee, M. S., et al., Nature 344:774-77, 1990. |
| Unknown-UL33 | Viral | Chee, M. S., et al., Nature 344:774-77, 1990. |

Although it is preferable to utilize the complete coding sequence from the G protein linked receptor gene, within certain embodiments of the invention only that portion of the G protein linked receptor gene which encodes expression of the receptor on the cell surface need be utilized. Within the context of the present invention, both the entire coding region and portions thereof are referred to as "G protein linked receptor genes." Such expression can be determined by any one of several suitable means, including ligand binding assays.

The coding sequence for the G protein linked receptor should be inserted in such a manner that the resulting recombinant Herpesvirus genome directs the synthesis of a transcript that is capable of being translated into a G protein linked receptor protein. The desired G protein linked receptor produced should be compatible with Herpesvirus propagation (i.e., is not lethal). The promoter sequence can be supplied within a separate or the same nucleic acid segment as the G protein linked receptor sequence or by the genomic portion of the recombinant virus. Suitable promoters include any one of several which are capable of initiating expression of the G protein receptor gene. Preferably, the promoter is a major immediate early promoter and the sequence includes a polyadenylation site. More preferably, the promoter is the cytomegalovirus (CMV) promoter.

In a preferred embodiment of the present invention, the Herpesvirus utilized is deficient for expression of the thymidine kinase (TK) gene locus (TK(−)). More preferably, the G protein linked receptor sequence is inserted in the thymidine kinase (TK) gene locus of an HSV-1 genome, rendering it deficient. Within the context of the present invention, "deficient" refers to low or nonexistent expression of the gene in question. Deficient expression generally results from insertion into or deletion of the genetic loci in question. Deficiency of the thymidine kinase loci can be assayed using any one of several means, including selection with bromodeoxyctidine using standard methods (see also Summers et al., *PNAS* 72:4081, 1975).

In another preferred embodiment of the present invention, the Herpesvirus genome is deficient for the expression of virion host shut off gene (UL41) locus and the thymidine kinase (TK) gene locus. Even more preferably, a nucleic acid segment encoding beta-galactosidase is inserted in the virion host shut-off gene (UL41) locus to allow for easy confirmation of successful debilitation and the G protein linked receptor sequence is inserted in the thymidine kinase (TK) gene locus. The deficiency in UL41 expression may be assayed for by detecting beta-galactosidase expression using standard techniques (see also Smibert et al., *J. Vir.* 68:2339, 1994).

In another aspect of the present invention, the Herpesvirus genome is additionally deficient in the expression of a viral gene required for replication ("replication deficient"). Briefly, proteins required for replication include, by way of example, ICP4 and DNA polymerase. Preferably, it is replication deficient in the expression of the ICP4 protein. Replication deficiency can be assayed using any one of several standard methods, including by comparison of cultures in complementary and noncomplementary cell lines (see also DeLuca et al., *J. Vir.* 56:558–570, 1985).

In another embodiment of the present invention, HSV-1 is provided which is both replication deficient and deficient in the expression of a viral host shut off gene (UL41) locus. Even more preferably, it is deficient in the expression of both UL41 loci and ICP4 protein.

Figure 1B:
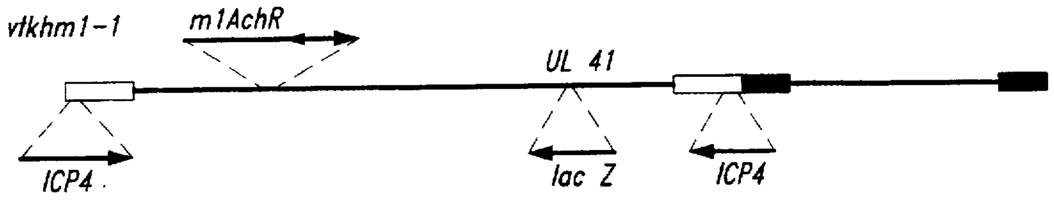
FIG. 1*b* is a schematic illustration of vTKhm1-1.
Figure 1C:
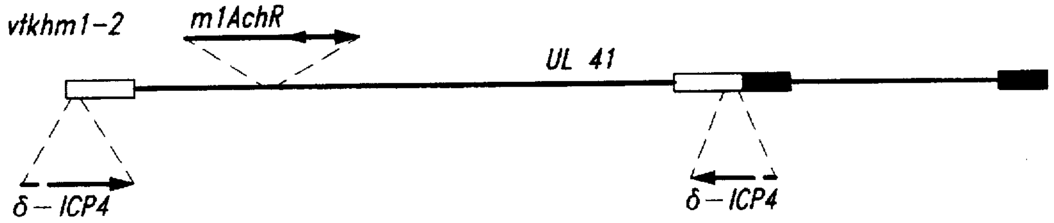
FIG. 1*c* is a schematic illustration of vTKhm1-2.
Figure 1D:
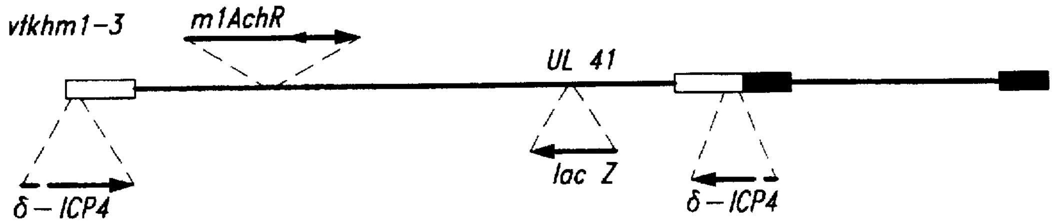
FIG. 1*d* is a schematic illustration of vTKhm1-3.

Within the context of the present invention, "vTKhm1-1" refers to a recombinant Herpesvirus vector which is deficient in both the expression of the viral host shut off protein (VHS) and thymidine kinase (TK). (FIG. 1b); "vTKhm1-2" refers to a recombinant Herpesvirus vector which is deficient in the expression of both the viral transcriptional regulator (ICP4) and thymidine kinase (TK). (FIG. 1c); and "vTKhm1-3" refers to a recombinant Herpesvirus vector which is deficient in both the expression of the viral transcriptional regulator, ICP4, VHS, and thymidine kinase (TK). (FIG. 1d). All three of the recombinant viruses express a G protein linked receptor (preferably inserted in the TK locus) from an immediate early promoter, preferably a CMV promoter. As described in more detail below, these recombinant Herpesvirus vectors are characterized by low cytopathicity and a high rate of expression. Recombinant Herpesvirus vectors with "essentially the same characteristics" is intended to refer to recombinant Herpesvirus vectors with the same or similar deficiencies in expression.

These and other recombinant Herpesvirus vectors characterized by low cytopathicity and/or a high level of expression of G protein linked receptor may be produced by culturing a first and second recombinant Herpesvirus in a suitable cell line for a time sufficient and under suitable conditions to allow for recombination. The first recombinant Herpesvirus is one carrying a G protein linked receptor gene and capable of expression thereof and the second recombinant Herpesvirus is replication deficient.

The G protein linked receptor nucleic acid segment may be inserted into the first recombinant Herpesvirus by any suitable means described above, including homologous recombination between the virus and a plasmid carrying the G protein linked receptor nucleic acid segment. Recombinant Herpesvirus vectors carrying the G protein linked receptor sequence may then be selected for using standard methods, including restriction digestion followed by Southern Blot hybridization. Preferably, the first recombinant Herpesvirus is TK(−) HSV-1. Even more preferably, the G protein linked receptor gene is inserted in the TK locus of the first recombinant Herpesvirus. Additionally, the first recombinant Herpesvirus is preferably deficient in expression in the virion host shut-off protein (VHS). Most preferably, the first recombinant virus is vhsA (J. Smiley, McMaster University, Hamilton Ontario) (FIG. 1A). Briefly, vhsA is a mutant HSV-1 which bears the beta-galactosidase gene in the UL41 region of its genome, rendering it deficient in expression of the virion host shut-off protein. The G protein linked receptor gene may be inserted into vhsA by the means described above.

Preferably, the second recombinant Herpesvirus vector is replication deficient. Even more preferably the second recombinant Herpesvirus vector is deficient in the expression of the ICP4 protein. Most preferably, the second recombinant HSV-1 is d120. (Disclosed in detail in DeLuca et al., "Isolation and Characterization of Deletion Mutants of Herpes Simplex Virus Type I in Gene Encoding Immediate Early Regulatory Protein ICP4," *J. Vir.* 56:558–570, 1985). Briefly, d120 is replication deficient HSV-1, due to diminished expression of ICP4. Recombinants defective for ICP4 expression may be selected using any one of several suitable methods noted above including Southern blot analysis, Northern blot analysis, or immunofluorescence studies.

If both the first and the second recombinant Herpesviruses are replication deficient, the two recombinant Herpesviruses can be transfected on a complementary cell line for replication. Suitable complementary cell lines include E5 Vero cells (ICP4(+)). (Disclosed in detail in DeLuca et al., "Isolation and Characterization of Deletion Mutants of Herpes Simplex Virus Type I in Gene Encoding Immediate Early Regulatory Protein ICP4," J Vir. 56:558–570, 1985).

The recombinant Herpesvirus vector resulting from the transfection of the first and second recombinant Herpesviruses may be selected for one or more of four basic characteristics: (1) thymidine kinase deficiency, (2) ICP4 expression, (3) UL41 expression, and (4) G protein receptor gene expression, using any one of several suitable methods described above. By way of example, thymidine kinase expression can be screened for using bromodeoxycytidine; ICP4 expression can be screened for based on the virus' ability or inability to grow on the complementing cell lines; UL41 expression can be screened for based on beta-galactosidase production; and expression of the G protein linked receptor gene can be screened for based a on ribonuclease protection assay. Maniatis et al., *Molecular Cloning, A Laboratory Manual*, Cold Spring Harbor Laboratory, Cold Spring Harbor, N.Y. (1982). Thus, three preferred embodiments of the invention vTKhm1-1(FIG. 1b), vTKhm1-2 (FIG. 1c), and vTKhm1-3 (FIG. 1d) may be produced and screened according to expression. The more preferred embodiment is vTKhm1-3 (FIG. 1d).

As noted above, within other aspects of the present invention, recombinant Herpesvirus vectors can be used to deliver G protein linked receptor nucleic acid sequence to mammalian cells. Once infected, the recombinant Herpesvirus vector will then produce the desired receptors which are expressed on the cell surface. The infected cells are then selected for the desired G protein linked receptor expression. For virus infection, the recombinant Herpesvirus vectors may be applied to the cells under standard cell culture conditions. Cell culture techniques are described in Maniatis et al., *Molecular Cloning, A Laboratory Manual*, Cold Spring Harbor Laboratory, Cold Spring Harbor, N.Y. (1982). The specific host cells employed in the present invention are not critical as long as they allow replication and expression of the recombinant Herpesvirus vectors. Suitable cells include Vero cells (ATCC Accession No. CRL 1587).

To select for the expression of G protein linked receptors, standard techniques may be employed, including ribonuclease protection assays such as those described in Maniatis et al., Molecular Cloning, A Laboratory Manual, Cold Spring Harbor Laboratory, Cold Spring Harbor, N.Y. (1982). Briefly, a labeled RNA probe is synthesized that is partially complementary to the region of the target mRNA. This labeled RNA probe is added to samples of the total cellular RNAs isolated from the cell culture after post infection by the recombinant virus. The mixture is incubated, for a sufficient time and under suitable conditions to enable a labeled probe to hybridize to the complementary RNAs and then subjected to digestion by suitable restriction enzymes, such as RNase A and RNase T1. Labeled probe that hybridized to complementary transcripts will be protected from digestion and may be separated on a polyacrylamide gel and viewed by autoradiography.

G linked protein receptor expression resulting from the insertion of the recombinant viruses of the instant invention into the cell can be detected using any one of several methods known in the art, including for example, ligand binding assays. Representative ligand binding assays suitable for use within the present invention include those described in Conn, *Methods in Neurosciences* (Vol. 9), "Gene Expression in Neural Tissues" Academic Press, Inc., San Diego, Calif. (1992). For example, within one embodiment the cells infected with the recombinant virus are incubated with a radiolabeled antagonist. Saturation curves may then be performed in order to determine the approximate number of receptors (represented by counts measured using the antagonist and competitive inhibition). Within other embodiments, stimulation of second messenger systems maybe be ascertained by any one of several suitable means, including, for example, phosphatidylinositol (PI) turnover assays.

The recombinant viruses of the present invention may be characterized in a variety of manners, including for example, by the number of receptors expressed on cells infected with the virus, the in vivo cytopathicity of the virus, and/or the immunogenicity of the virus. For example, within certain embodiments of the present invention, recombinant Herpesvirus vectors are provided which express greater than about 10,000 receptors per cell, preferably between about 25,000–200,000 receptors per cell, more preferably greater than about 200,000 receptors per cell and most preferably between about 200,000 to 400,000 receptors per cell, or even greater than about 400,000 receptors per cell. Within other embodiments, recombinant viruses are provided which have an in vivo cytopathicity of generally less than the in vitro cytopathicity. "Cytopathicity" as used herein, refers to cell survival five days after infection. Cytopathicity may be measured using any one of a wide variety of techniques known in the art, including commercially available kits. Suitable kits include Live/Dead™ (Molecular Probes Inc.; viability/cytotoxicity kit utilizing a method of staining).

By way of example, vTKhm1-1 is characterized by a surface receptor expression rate generally greater than 10,000 receptors per cell; typically in about the range of 60,000 to 80,000; and preferably in about the range of 70,000 to 100,000.

vTKhm1-2 is characterized by a cytopathicity of generally less than 50%; typically in about the range of 35%–40%; and preferably in about the range of 20%–35%. vTKhm1-2 is further characterized by surface receptor expression generally greater than 80,000; typically in about the range of 120,000–160,000; and preferably in about the range of 160,000 to 200,000.

vTKhm1-3 is characterized by a cytopathicity of about in vitro cytopathicity of less than about 3%, typically in about the range of 0.1% to 1.0% and preferably in about the range of 0.001%–0.1%. vTKhm1-3 is further characterized by surface receptor expression generally greater than 800,000 receptors, typically in the range of 1–1.5 million receptors, and preferably 1.25–2 million receptors/cell.

ADDITIONAL METHODS AND COMPOSITIONS

Within other aspects of the invention, methods are provided for producing a protein of interest, comprising the steps of introducing an expression cassette or gene delivery construct as described above, into a host cell, and culturing the hot cell under conditions, and for a time sufficient to permit expression of the protein. The expression cassettes may be introduced by a wide variety of mechanisms, including for example, including for example calcium phosphate-mediated transfection (Wigler et al., *Cell* 14:725, 1978), lipofection; gene gun (Corsaro and Pearson, *Somatic Cell Gen.* 7:603, 1981; Graham and Van der Eb, *Virology* 52:456, 1973), electroporation (Neumann et al., *EMBO J.* 1:841–845, 1982), protoplast fusion-mediated transfection or DEAE-dextran mediated transfection (Ausubel et al., (eds.), *Current Protocols in Molecular Biology*, John Wiley and Sons, Inc., New York, N.Y., 1987).

Optionally, the resultant protein may be purified by a variety of methods, including for example, within one embodiment cell supernatant may be first concentrated using commercially available protein concentration filters, such as an Amicon or Millipore Pellicon ultrafiltration unit. Following concentration, the concentrate may be applied to a suitable purification matrix, or alternatively, purified utilized anion or cation exchange resins. Finally, one or more reversed-phase high performance liquid chromatography (RP-HPLC) steps may be employed.

Expression cassettes or gene delivery constructs of the present invention may also be utilized to introduce a selected sequence of interest into an in vitro culture containing neuronal cells, comprising the step of introducing an expression cassette or gene delivery construct, as described herein, into an in vitro culture of cells containing neuronal cells.

In another aspect of the present invention, and using the techniques described above, the gene delivery constructs or recombinant viruses of the present invention can also be packaged in a suitable cell line. For example, within one embodiment of the invention, recombinant HSV-1 is cultured ex vivo in suitable mammalian cells. These cells may then be introduced in vivo, using the techniques describe below, ie., stereotactical microinjection, for treatment of neurological disorders or analysis. Alternatively, the expression cassette or gene delivery construct may be introduced directly in vivo by any one of several methods described below.

In another aspect of the present invention, the expression cassettes or gene delivery constructs described above are administered to a warm-blooded animal (e.g., a human, monkey, cow, sheep, dog, cat, rat or mouse), or other-type of animal (e.g., fish) for the treatment of neuronal cell disorders, in both the central and peripheral nervous system. Such cassettes or constructs may be utilized in the treatment of a wide variety of disorders, including for example, brain tumors, degenerative disorders, neural disorders characterized by abnormal gene expression, and inherited disorders.

The expression cassettes or gene delivery constructs of the present invention may also be utilized to deliver normal genes. This allows for the treatment of deficiency state disorders, usually of enzymes, by increasing production thereof.

Additionally, the recombinant virus can be used to decrease the production thereof by using antisense sequences. This is useful in creating animal models for the deficiency disorders or treating over expressive disorders. For example, expression cassettes of the present invention may be utilized to express sequences of interest in non-human transgenic animals such as mice, rats, rabbits, sheep, dogs and pigs (see Hammer et al. (*Nature* 315:680–683, 1985), Palmiter et al. (*Science* 222:809–814, 1983), Brinster et al. (*Proc. Natl. Acad. Sci. USA* 82:4438–4442, 1985), Palmiter and Brinster (*Cell* 41:343–345, 1985) and U.S. Pat. No. 4,736,866). For example, within one embodiment an expression cassette may be introduced into pronuclei of fertilized eggs, for example, by microinjection. Integration of the injected DNA may be detected by blot analysis of DNA from tissue samples. It is preferred that the introduced DNA be incorporated into the germ line of the animal so that it is passed on to the animal's progeny. Such techniques allow for, within preferred embodiments, tissue-specific (e.g., neuronal cell) expression of a desired sequence of interest.

The expression cassettes or gene delivery constructs of the present invention may also be used to create unbalanced state disorders involving structural or regulatory proteins, in a model system, which could be used in efforts to establish and study methods of counteracting the effect of the imbalance.

In one aspect of the present invention, expression cassettes or gene delivery constructs may be used to treat neurodegenerative disorders including, by way of examples, Alzheimer's disease, Spinal muscular Ataxia, mytonic dystrophy, Spinal Balbar Muscular Atrophy (SBMA), Kennedy syndrome, Parkinson's disease, Senile dementia, Circumscribed cerebral atrophy, Huntington's chorea, Cerebrocerebellar degeneration, Amaurotic family idiocy, Leukodystrophy, Familial myoclonus epilepsy, Hallervorden-Spatz disease, Wilson's disease, hepatolenticular degeneration, Westphal-Strumpell pseudosclerosis, Paralysis agitans, Dystonia musculorum deformans, torsion dystonia, Hallervorden-Spatz disease, Spasmodic torticollis, Cerebellar degenerations, Spinocerebellar degenerations, Friedrich's ataxia, Marie's hereditary ataxia, Amyotrophic lateral sclerosis, Progressive muscular atrophy, Progressive bulbar palsy, Primary lateral sclerosis, Werdnig-Hoffmann disease, Wohlfart-Kugelberg-Welander syndrome, Hereditary spastic paraplegia, Progressive neural muscular atrophy, Peroneal muscular atrophy (Charcot-Marie-Tooth) Hypertrophic interstitial neuropathy (Dejerine-Sottas), Leber's disease, retinitis pigmentosa and fragile X disorder.

In another aspect of the present invention, expression cassettes or gene delivery constructs may be used to treat disorders characterized by abnormal gene expression, and inherited disorders caused by a known gene defect. In addition to a number of the disorders listed above, genes for defective enzymes or proteins have been identified, by way of example, for (1) lysosomal storage disorders such as those involving β-hexosaminidase (Kornerluk et al., *J. Biol. Chem.* 261:8407–8413, 1986); Myerowitz et al., *Proc, Natl. Acad. Sci.* (*USA*) 82:5442–5445, 1985); Tsuji et al., *N. Engl. J. Med.* 316:570–575, 1987), (2) for deficiencies in hypoxanthine phosphoribosyl transferase activity (the "Lesch-Nyhan" syndrome; Stout et al., *Met. Enzymol.* 151:519–530, 1987), (3) for amyloid polyneuropathies (prealbumin; Sasaki et al., *Biochem. Biophys. Res. Commun.* 125:636–642, 1984), (4) for Alzheimer's Disease (see, for example, Gont et al., *Nature* 349:704, 1991; Sherrington et al., *Nature* 375:754, 1995; Levy-Labad et al., *Science* 269:973, 1995; Tanzi et al., *Science* 235:880–884, 1987; Goldgaber et al., *Science* 235:877–880, 1986), (5) for Duchenne's muscular dystrophy (uncharacterized muscle protein; Monaco et al., Nature 323:646–650, 1987), and (6) for retinoblastoma (uncharacterized protein expressed in the retina and other tissues, Lee et al., *Science* 235:1394–1399, 1987; Friend et al., *Nature* 323:643–646, 1986).

Expression cassettes and gene delivery constructs may also be used to study the "shiverer" mutation (myelin basic protein, Roach et al., Cell 42:149–155 (1987); Molineaux et al., *Proc. Natl. Acad Sci.* (*USA*) 83:7542–7546 (1986), and the "jumpy" mutation (proteolipoprotein, Nave et al., *Proc. Natl. Acad Sci.* (*USA*) 83:9264–9268 (1986); Hudson et al., *Proc. Natl. Acad. Sci.* (*USA*) 84:1454–1458 (1987)).

Expression cassettes and gene delivery constructs of the present invention can also be used for treatment of acute injuries to the brain or peripheral nervous tissue, for example from a stroke, brain injury, or spinal cord injury.

Expression cassettes and gene delivery constructs of the present invention may also be used in the treatment of disorders which require receptor modulation to increase or decrease transmitter uptake. Such disorders include schizophrenia, obsessive-compulsive disorder, depression, and bipolar mood disorders.

As utilized within the context of the present invention, the term "treatment" refers to reducing or alleviating symptoms in a subject, preventing symptoms from worsening or progressing, inhibition or elimination of the causative agent, or prevention of the infection or disorder in a subject who is free therefrom. Thus, for example, treatment of infection includes destruction of the infecting agent, inhibition of or interference with its growth or maturation, neutralization of its pathological effects and the like. A disorder is "treated" by partially or wholly remedying the deficiency which causes the deficiency or which makes it more severe. An unbalanced state disorder is "treated" by partially or wholly remedying the imbalance which causes the disorder or which makes it more severe.

The expression cassettes or gene delivery constructs of the present invention may be administered by any one of several methods of administration known in the art which account for the risk of degradation of the recombinant virus in the bloodstream and such that the virus retains its structure and is capable of infecting target cells. Within one embodiment, administration may be accomplished by microinjection of the virus, alone or in a pharmaceutically suitable carrier or diluent, through a stereotactically-located pipette or syringe. Suitable locations vary with application, but include intraocular and brain injections.

Pharmaceutical carriers and diluents which are suitable for use within the present invention include, for example, water, lactose, starch, magnesium stearate, talc, gum arabic, gelatine, polyalkylene glycols (e.g., polyethylene glycol), and the like. The pharmaceutical preparation may be made up in liquid form for example, as solution, emulsion, suspension and the like or in a solid form, for example as a powder and the like.

If necessary, the pharmaceutical preparations can be subjected to conventional pharmaceutical adjuvants such as preserving agents, stabilizing agents, wetting agents, salts for varying the osmotic pressure, and the like. The present pharmaceutical preparations may also contain other therapeutically valuable substances.

In another aspect of the present invention, expression cassettes or the delivery constructs described herein may be delivered by chronic infusion using any suitable method known in the art, including an osmotic minipump (Alza Corp.) or delivery through a time release or sustained release medium. Suitable time release or sustained release systems include any methods known in the art, including media such as Elvax (or see, for example, U.S. Pat. Nos. 5,015,479, 4,088,798, 4,178,361, and 4,145,408). When using chronic infusion, time release, or sustained release mechanisms, the composition may be injected into the cerebrospinal fluid via intrathecal or intraventricular injections, as well as into the brain substances and intraocular locations.

The expression cassette or gene delivery construct should be administered in a therapeutically effective amount. A therapeutically effective amount is that sufficient to treat the disorder. A therapeutically effective amount can be determined by in vitro experiment followed by in vivo studies. Expression of the inserted nucleic acid segment can be determined in vitro using any one of the techniques described above. Expression of the inserted nucleic acid segment can be determined in vivo using any one of several methods known in the art, including immunofluorescence using a fluoresceinated ligand.

In another aspect of the present invention, the expression cassettes or gene delivery constructs described above may be incorporated into a pharmaceutical composition. Preferably, the pharmaceutical composition contains one or more therapeutically effective doses of the cassette or construct in a suitable pharmaceutical carrier or diluent. Suitable pharmaceutical carriers and diluents are outlined above. A therapeutically effective dose may be determined by in vitro experiment followed by in vivo studies as described above. The composition may be administered by any one of the methods described above.

The following examples are provided by way of illustration, and not by way of limitation. Unless otherwise indicated, the specific protocols used in the following examples are described in detail in Maniatis et al., supra, or Sambrook et al., supra.

EXAMPLE 1

Generation of a Recombinant Herpesvirus Vector Which Expresses m1Muscarinic Acetylcholine Receptor A recombinant Herpesvirus vector which expresses the m1 muscarinic acetylcholine receptor (m1-AchR) was generated by homologous recombination between an HSV-1 virus and a plasmid, pTKhm1, which was constructed for this purpose.

Briefly, pTKhm1 was prepared from the coding sequence for the human m1-AchR gene and altered pTKSB. The coding sequence of m1-AchR was isolated as a 2.7 kb BamHI fragment from a plasmid containing this sequence (Bonner et al., *Science* 237:527–532, 1987; see also generally Genbank Accession Nos.: M16404, M16405, M16406, M16407, M16408, M16409) and inserted into a plasmid vector containing a single BamHI cloning site. The coding sequence was re-isolated by digestion of that plasmid vector with EcoRI and HindIII.

pTKSB (Smiley et al., *J. Vir.* 61(8):2368–77 (1987)), which contains the HSV-1 TK gene, was altered by insertion of a CMV promoter-containing fragment from the plasmid pRc/CMV (Invitrogen Corporation). This fragment represents the portion of the plasmid extending from base 209 to base 1285 and containing the CMV major immediate early promoter, a multicloning site, and a poly A addition site. The fragment was inserted into pTKSB by first digesting the plasmid with BamHI and then converting the BamHI site into a PacI site by the addition of adapter sequences. The CMV promoter was oriented in the opposite direction to the TK promoter to reduce transcriptional interference. The resulting plasmid (pTKSB containing the CMV promoter) was then digested with EcoRI and HindIII and ligated to the m1-AchR coding sequence which had also been digested with HindIII and EcoRI using conventional methods. This plasmid was referred to as pTKhml.

pTKhm1 was then used to generate an HSV recombinant virus by in vivo homologous recombination. pTKhm1 was cotransfected into Vero cells (ATCC Accession No. CRL 1587) along with an infectious HSV-1, vhsA. vhsA is a mutant HSV-1 (FIG. 1*a*) (see Smibert and Smiley, *J. Vir.* 64:3882, 1990) containing the β-galactosidase gene in the UL41 gene coding sequence.

TK deficient recombinants were selected using bromodeoxycytidine. Following selection, virus isolates were plaque purified and tested for the CMV-m1-AchR insert by digestion with EcoRI, electrophoresis on a 1.1% agarose/TAE gel and hybridization to a radioactive probe. The probe was generated by incubating the m1Achr gene in buffer containing random hexamers of DNA to act as primers for extension by DNA polymerase in the presence of dGTP, dTTP, dATP, and 100 mCi [$^{32}$P] dCTP. After 3 h of incubation, the probe was used in hybridization at 37° C. in the presence of 50% formamide, 2X standard saline citrate, 5X Denhardt's solution, 1% sodium dodecyl sulfate. Following incubation for 12 h, filters were washed extensively in 0.2XSSC, 0.1% SDS, dried, and exposed to X-ray film until a signal was detected. One virus, referred to as vTkhm1 (FIG. 1*b*), lacked a 2.1 kb EcoRI fragment containing the endogenous TK gene and instead, contained a 4.6 kb EcoRI fragment which hybridized to the m1-AchR specific probe. Thus, it was determined that the neurotransmitter receptor gene was successfully introduced into the viral genome.

EXAMPLE 2

Detection of m1AchR mRNA Expression from Recombinant Viruses

Figure 2:
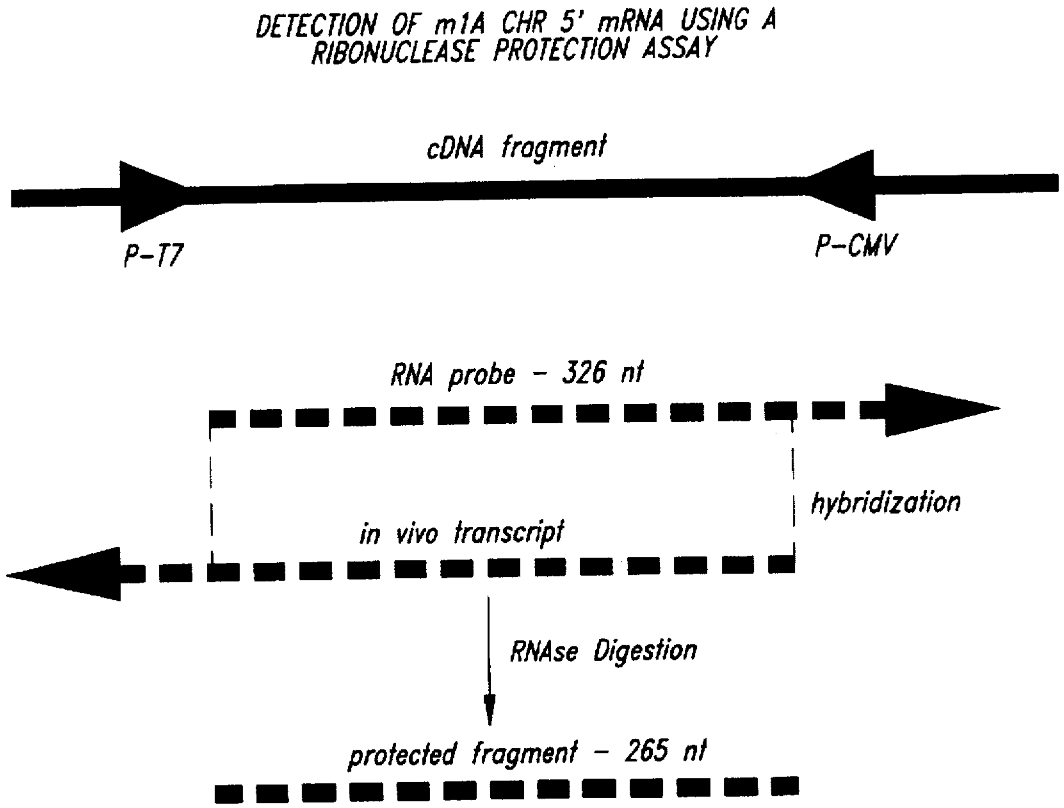
FIG. 2 is a schematic diagram illustrating the detection of m1ACHR5' mRNA using a ribonuclease protection assay.

Expression of m1AchR transcripts from the CMV promoter was detected using a ribonuclease protection assay. (FIG. 2). Briefly, a labeled RNA probe was synthesized from 326 nucleotides (nt) from the T7 promoter of the plasmid BS/KS(−) (available from Stratagene Cloning Systems) comprising 265 nt of the 5' end of the m1Achr gene and 56 nt of the 3' end of the CMV promoter. This probe targeted the 5' end of human m1AchR mRNA as well as a portion of the CMV promoter. This labeled probe was incubated with samples of total cellular RNAs isolated from Vero cells 2 to 18 hours post-infection (hpi) by vTKhm1.

Figure 3:
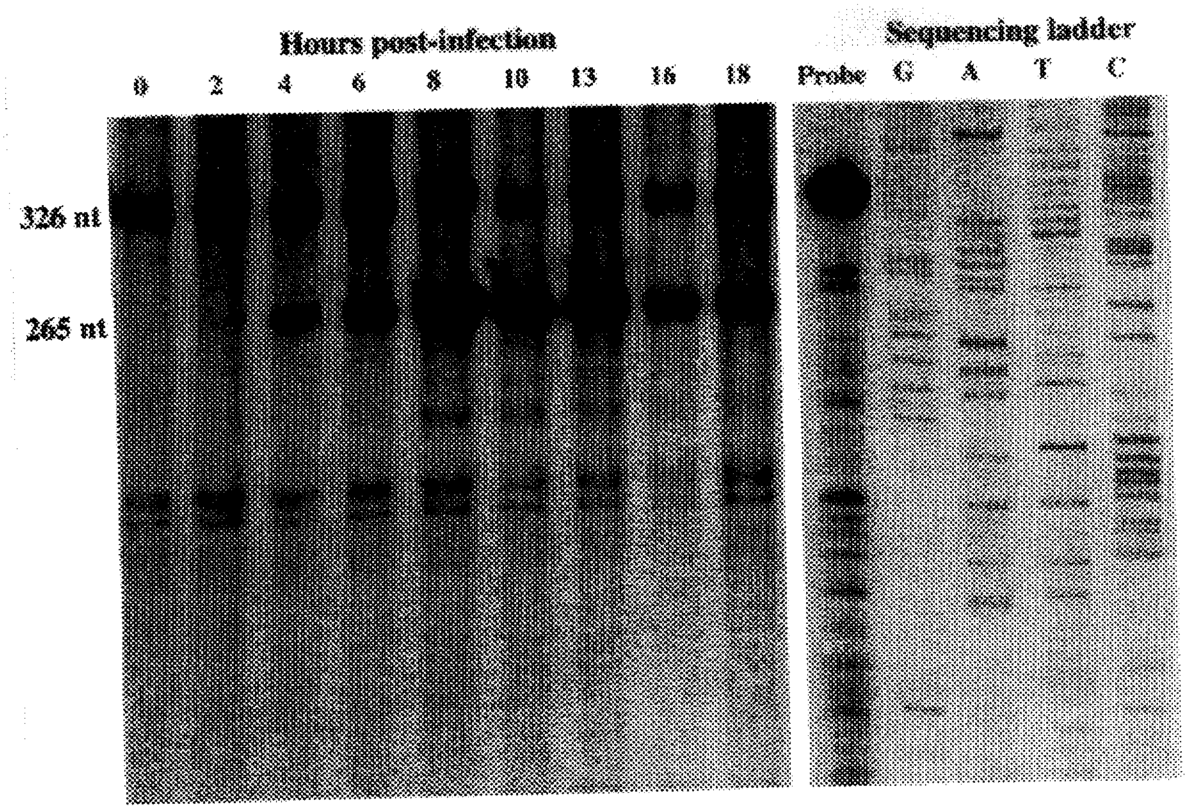
FIG. 3 is a photograph of a urea/polyacrylamide gel which shows labeled probe that had hybridized to cellular RNA was subsequently identified following electrophoresis on an 8M urea/polyacrylamide gel and visualized by autoradiography. A protected RNA fragment of 265 nt which corresponded to transcription of the insert from the CMV promoter was detected as early as 3 hours post infection ("hpi"), reached high levels by 8 hpi, and maintained high levels until 18 hpi. (See Example 2.)

The reaction was then subjected to digestion by RNaseA and RNaseT1 under conditions of high salt to inhibit digestion of double-strand RNA. Labeled probe that had hybridized to cellular RNA was subsequently identified following electrophoresis on an 8M urea/polyacrylamide gel and visualized by autoradiography. (FIG. 3). A protected RNA fragment of 265 nt which corresponded to transcription of the insert from the CMV promoter was detected as early as 3 hours post-infection ("hpi"), reached high levels by 8 hpi, and maintained high levels until 18 hpi. (FIG. 3).

EXAMPLE 3

Isolation of ICP4-Recombinants Expressing the m1AchR Gene

Recombinants were generated by homologous recombination between two viruses: d120, an ICP4(−) virus developed by DeLuca, (DeLuca et al., "Isolation and Characterization of Deletion Mutants of Herpes Simplex Virus Type I in Gene Encoding Immediate Early Regulatory Protein ICP4," *J. Vir.* 56:558–570, 1985), and vTKhm1 (FIG. 1*b*), prepared in Example 1. Briefly, the viruses were coinfected with E5 cells, an ICP4-expressing Vero cell line. The resulting virus stock was selected for TK(⁻) mutants with bromodeoxycytidine, and clones were screened for their ability to grow on E5 cells, but not Vero cells.

Positive clones were then tested for the presence of the m1AchR gene by restriction digestion with EcoRI and Southern blot hybridization. One virus clone, referred to as vTKhm1-2 (FIG. 1*c*), was found to both express m1AchR and form plaques only with E5 cells.

This recombinant was then used to generate a third recombinant, referred to as vTKhm1-3 (FIG. 1*d*), which is defective in both ICP4 and VHS expression. E5 cells were coinfected with vTKhm1-2 (FIG. 1*c*) and vhsA, the HSV-1 mutant that expresses β-galactosidase from its UL41 region. Bromodeoxycytidine was used to select against vhsA, and the resulting viral isolates were screened (a) for their ability to grow on E5 cells, but not Vero cells, (b) for the expression of m1AchRs, and (c) for the expression of β-galactosidase. These recombinants were referred to as vTKhm1-3 (FIG. 1*d*).

EXAMPLE 4

Figure 4:
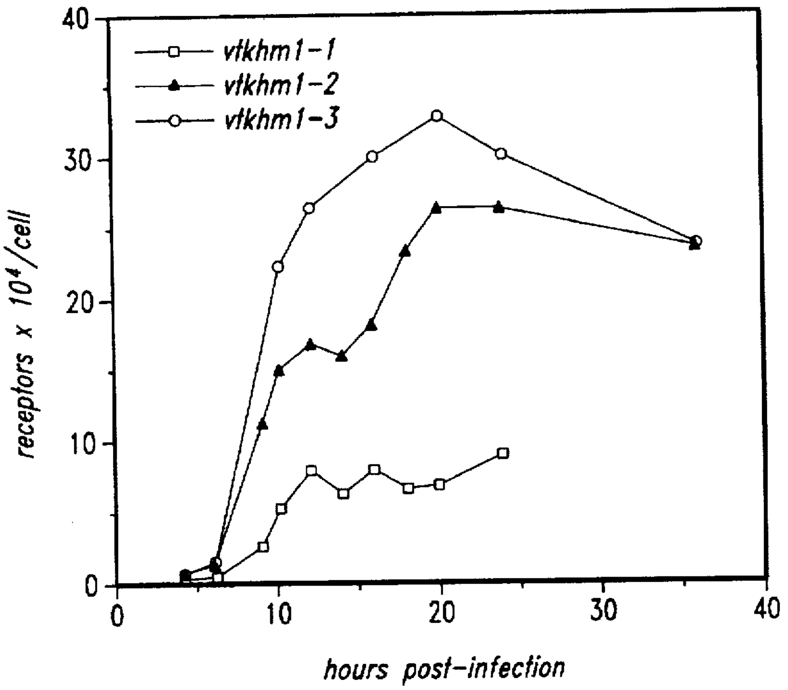
FIG. 4 is a graph which shows saturation curves representing the number of m1AchR expressed per Vero cell in samples harvested 2 to 36 hours post-infection (hpi) in samples infected with one of the following: vTKhm1-1, vTKhm1-2, and vTKhm1-3.

Detection of Surface Receptor Expression From Recombinant Viruses in Vero Cells Using Ligand Binding Assays The expression of m1AchR from Vero cells infected with a multiplicity of infection of 10 with vTKhm1-1, vTKhm1-2 and vTKhm1-3 was compared using the [$^3$H]NMS ligand binding assay. Surface m1AchR were measured by incubating infected Vero cells with 1 nM of the radiolabeled muscarinic receptor antagonist, n-methyl-scopolamine ([$^3$H] NMS) at 37° C. for 1 hour. After incubation with [$^3$H]NMS, the infected cells were washed three times with phosphate buffered saline, lysed and counted in scintillation fluid. Saturation curves were performed to determine the approximate number of m1AchRs represented by counts measured using 1nM [$^3$H]NMS. (FIG. 4). Competitive inhibition by pirenzepine confirmed that these counts reflect specific binding of the ligand to m1AchRs.

Vero cells do not contain any endogenous m1AchRs, therefore any [$^3$H]NMS binding above background represent receptors expressed from the recombinant virus. The expression of m1AchRs from each recombinant is shown. (FIG. 4). The ICP4-mutant, vTKhm1-2 infected Vero cells expressed 2–3 fold more m1AchRs than the VHS-mutant, vTKhm1-1 infected Vero cells. Vero cells infected with the triple mutant, vTKhm1-3, expressed greater than 5-fold more receptors than those infected with vTKhm1-1 and at least 2-fold more than those infected with vTKhm1-2 in the first 12 hours following infection. After 20 hpi, m1AchR surface expression appears to plateau. At 36 hpi m1AchR surface expression from vTKhm1-2 and vTKhm1-3 are approximately the same. Receptor expression from vTKhm1 plateaus by approximately 12 hpi, and by 36 hpi Vero cells infected with the replication competent vTKhm1-1 recombinant are dead.

EXAMPLE 5

Figure 5:
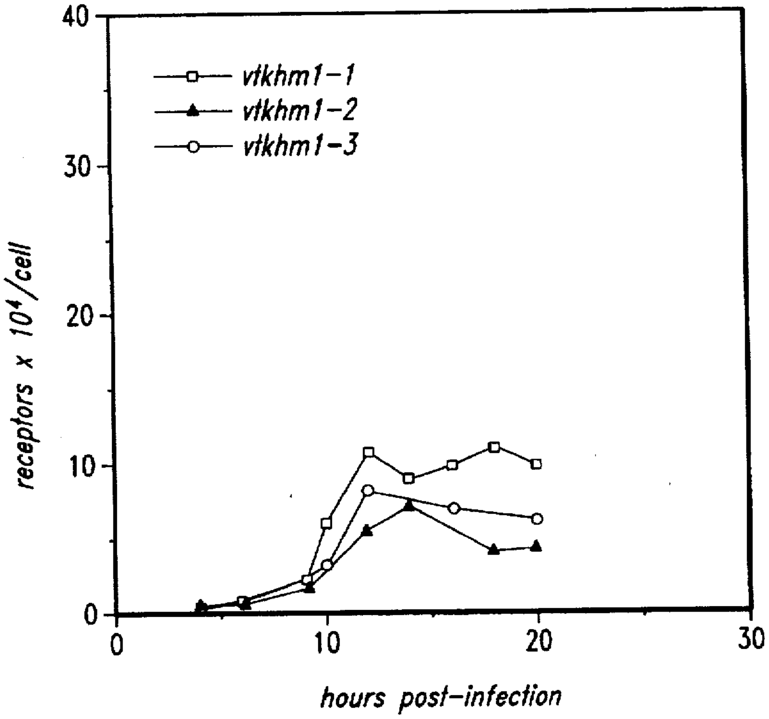
FIG. 5 is a graph which shows saturation curves representing the number of m1AchR expressed in transfected E5 cells in samples harvested 2 to 20 hours post-infection (hpi) in samples infected with one of the following: vTKhm1-1, vTKhm1-2, and vTKhm1-3.
Figure 11:
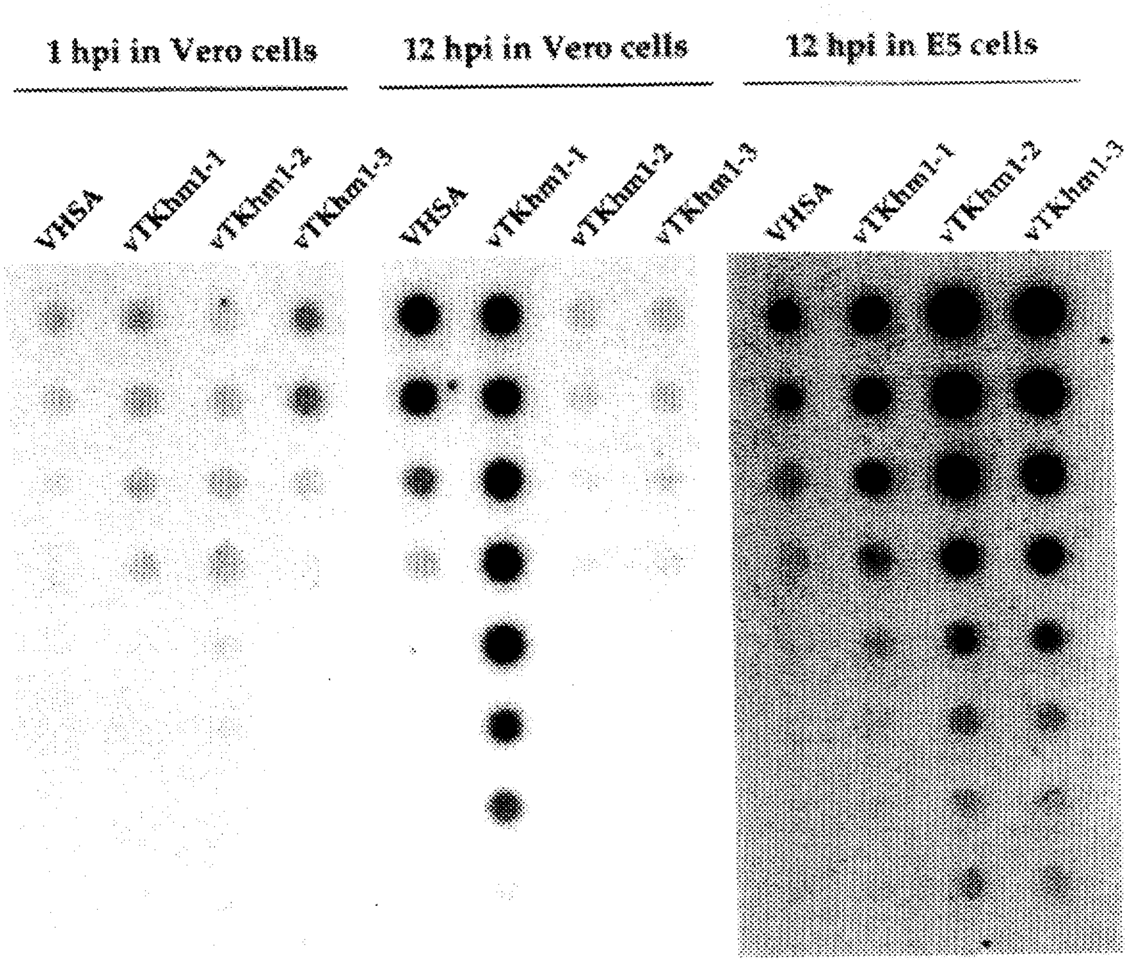
FIG. 11 is a photograph of a DNA replication assay confirming the phenotype of each strain of virus. Briefly, the results of this assay show that vTKhm1-2 and vTKhm1-3 do not replicate in normal Vero cells, but do replicate in E5 cells, which express ICP4 and complement the defect in the virus.

Detection of Surface Receptor Expression From Recombinant Viruses in E5 Cells Using Ligand Binding Assays The expression of m1AchR from E5 cells, ICP4(−) Vero cells, infected with a multiplicity of infection of 10 with vTKhm1-1, vTKhm1-2 and vTKhm1-3 was compared using the same [$^3$H]NMS ligand binding assay as in Example 4. (FIG. 5). Complementation of the ICP4(⁻) mutation in vTKhm1-2 and vTKhm1-3 transfected E5 cells results in drastically reduced levels of m1AchRs. (FIG. 5). These results indicate that the increased expression levels in vTKhm1-2 and vTKhm1-3 infected Vero cells is related to lack of ICP4 expression. The expression of ICP4 by the E5 cells allows the recombinant viruses to replicate. (FIG. 11). This data further indicates that the lack of viral host-protein synthesis (VHS) expression contributes to increased m1AchR expression, since vTKhm1-1 and vTKhm1-3 have higher expression levels than vTKhm1-2 in E5 cells.

At 1 hpi and 12 hpi DNA was isolated from each of the infected Vero and E5 cell samples by standard methods and dotted onto nitrocellulose membrane in three fold dilutions. (FIG. 11) vhsA infected Vero and E5 cell samples served as a control. These results demonstrate that vTKhm1-2 and vTKhm1-3 samples replicated in the E5 cell samples, but not in the Vero cell samples.

EXAMPLE 6

Confirmation of Defective ICP4 Expression in vTKhm1-2 and vTKhm1-3

Figure 9:
FIG. 9 is a photograph which shows a field of primary mouse cortical neurons growing on glass coverslips infected with vTKhm1-3. Briefly, cells growing on glass coverslips were rinsed with isotonic saline and fixed with 3.2% formaldehyde for 10 min at room temperature. Cells were rinsed and permeabilized with 0.3% Triton X-100 for 3 min at room temperature. Cells were then rinsed and incubated in primary antibody for 1 h, rinsed three times with saline, and incubated with fluorescent antibodies for 1 h at room temperature. Following this incubation, cells were rinsed, mounted on a glass slide and viewed using an epifluorescence microscope with barrier filters to distinguish green from red fluorescence. The green signal is derived from fluorescein-isothiocyanate conjugated goat anti-rabbit antibody non-covalently attached to the primary rabbit polyclonal antiserum anti-enolase. The orange signal is derived from tetramethyl rhodamine isothiocyanate conjugated goat anti-mouse antibody attached non-covalently to a mouse monoclonal antibody directed against the herpes protein ICPO.
Figure 10:
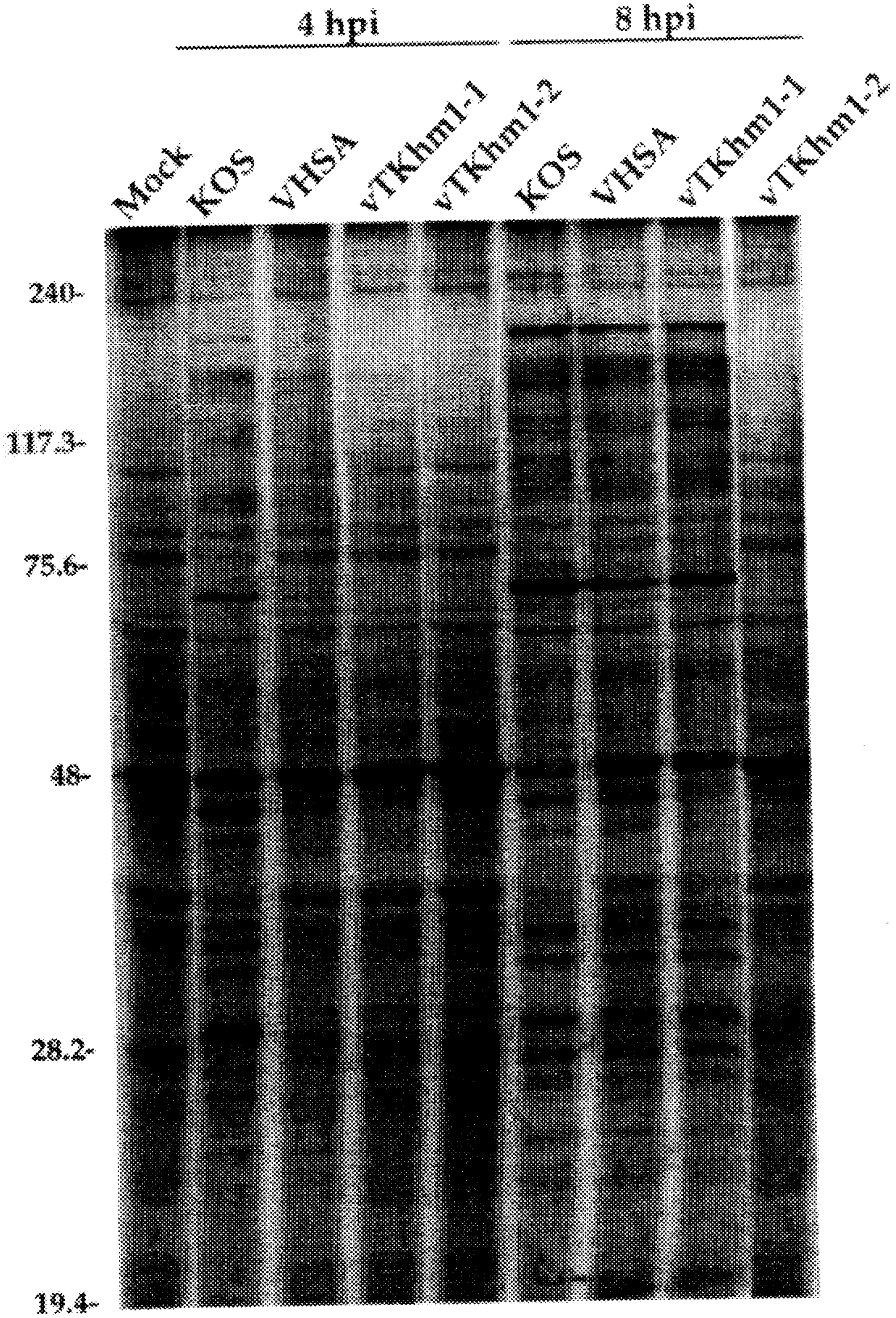
FIG. 10 is a photograph of a gel which shows protein synthesis in infected cells demonstrating that vTKhm1-2, which is the backbone vector for vTKhm1-3 and vTKhm1-1, does not alter protein synthesis after infection. Monolayers of Vero cells were infected with virus for 1 h at 38° C., and rinsed with growth medium. Cells were then incubated with growth medium lacking cold methionine. After 30 min, 100 mCi/ml [35S] methionine was added for the remainder of the experiment. Cells monolayers were harvested in detergent buffers and proteins were identified on SDS gels.

Southern blot analysis and immunofluorescence studies were performed to ensure that the recombinants, vTKhm1-2 and vTKhm1-3, were defective in ICP4 expression. Southern blot confirmed the presence of a 4.05 kb deletion in ICP4. This deletion is characteristic of d120, the ICP4(⁻) HSV-1 strain used to construct these recombinants. The expression of the ICP4 product in Vero cells infected with the HSV-1 recombinants was assayed by indirect immunofluorescence using a monoclonal antibody directed against ICP4. Fluorescence micrographs of Vero cells infected with either (a) vTKhm1-1, (b) vTKhm1-2 or (c) vTKhm-3 at 4 hours post-infection were produced. The ICP4 antigen could only be detected in Vero cells infected with vTKhm1-1;

vTKhm1-2 and vTKhm1-3 infected Vero cells did not express detectable amounts of ICP4. (FIG. 9).

EXAMPLE 7

Figure 7:
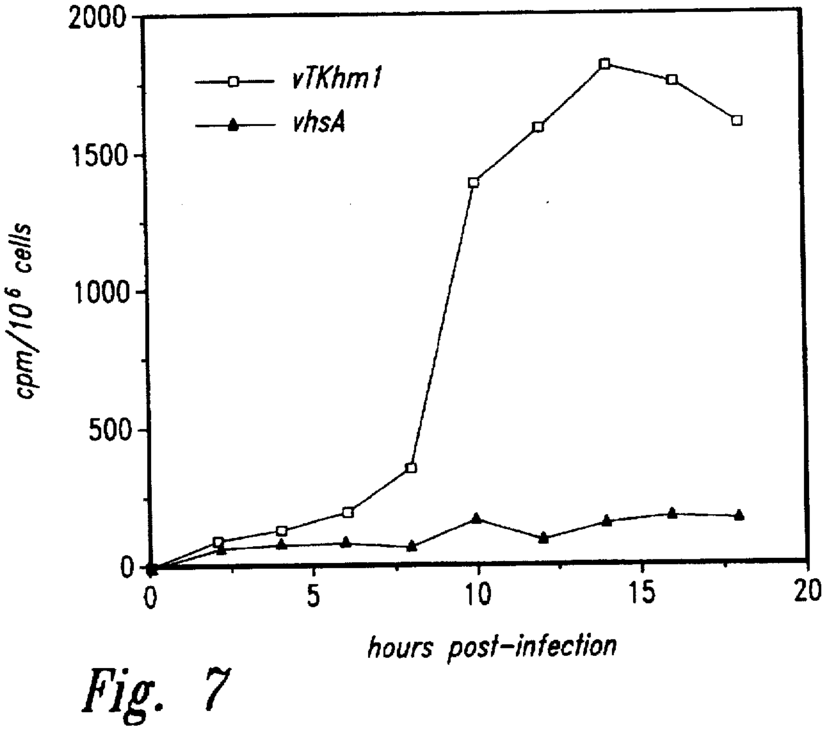
FIG. 7 is a graph which shows saturation curves representing a comparison of receptor binding of vhsA to vTKhm1-1.
Figure 8:
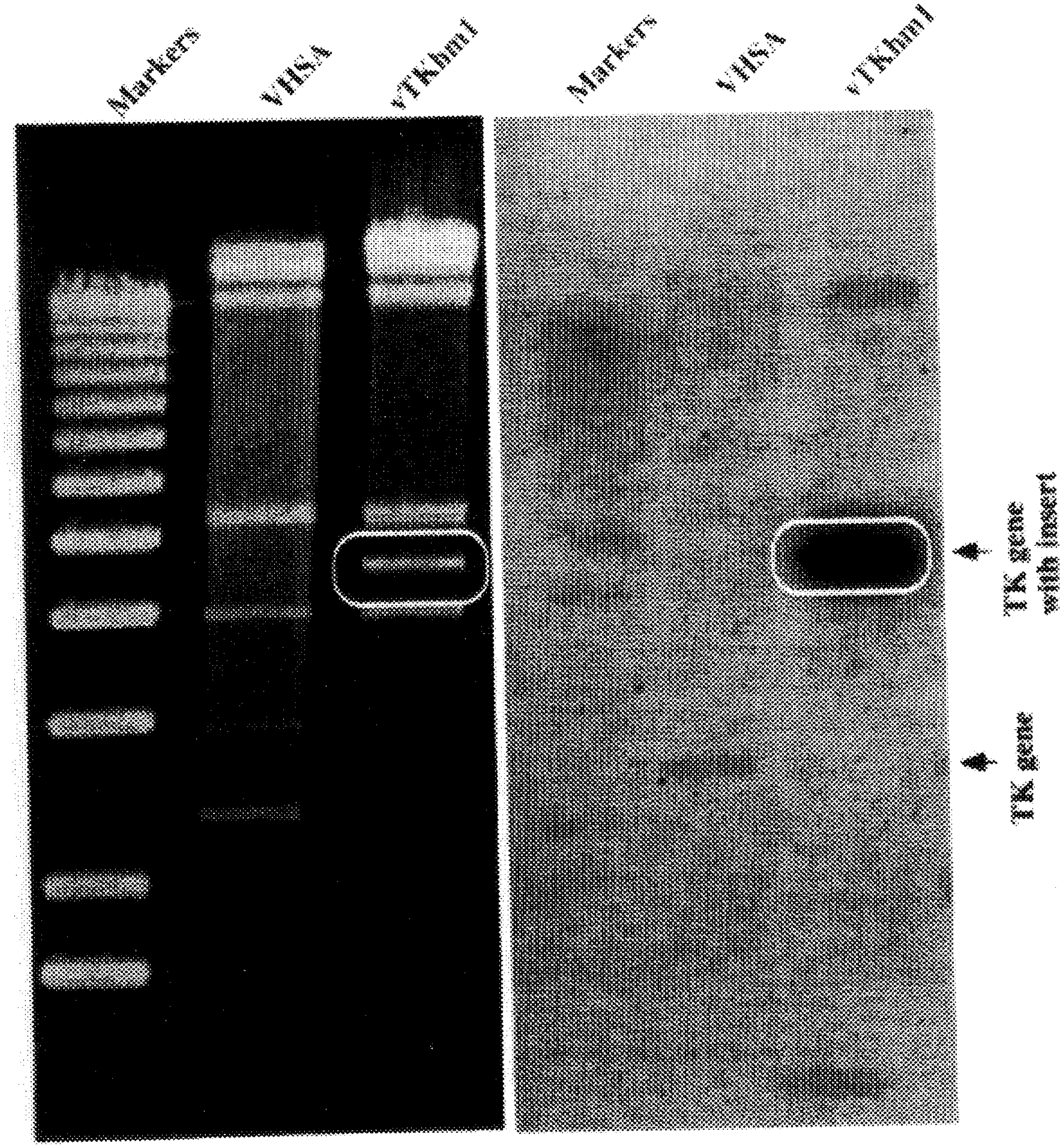
FIG. 8 is a photograph of a southern blot of viral DNA, comparing vhsA and vTKhm1-1.

Expression of m1AchRs From HSV-1 Recombinants in Primary Cortical Neuron Cultures Primary cortical neuron cultures, isolated from seven-day-old neonatal rats, were infected with either vTKhm1-1, vTKhm1-2, or vhsA at a multiple of infection of 3. At 12 hpi, the cultures were incubated at 37° C. with [$^3$H]NMS for 1 hour. In addition, uninfected control cultures were assayed to measure the amount of endogenous m1AchR expressed in primary cortical neuron cultures. Atropine, an m1AchR antagonist which competes with [$^3$H]NMS binding, was used to determine the amount of nonspecific ligand binding present in each sample. (FIG. 7).

Figure 6:
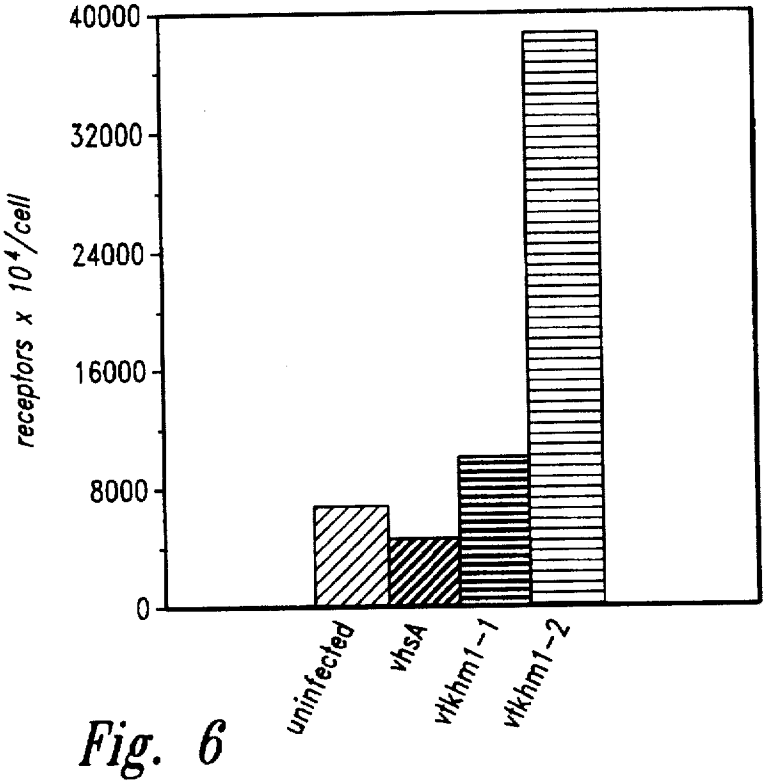
FIG. 6 is a bar graph which shows the number of m1AchR expressed in primary cortical neuron cultures at 12 hpi for vhsA, vTKhm1-1, vTKhm1-2, and uninfected Vero cells.

In these assays, vTKhm1-2 infected cells expressed 5 fold more m1AchRs than uninfected cultures, or approximately 38,000 surface receptors per cell as compared to 6,000 receptors on an uninfected cell. (FIG. 6). However, cells infected with vTKhm1-1 expressed less than a 2-fold increase in the amount of m1AchR compared to uninfected cultures. (FIG. 6). vhsA infected cultures expressed fewer receptors than the uninfected cultures. (FIG. 6). Moreover, there were no cytopathic effects evident in either vTKhm1-2 infected neurons or the vTKhm1-1 infected neurons. These results demonstrate that the recombinant viruses of the present invention reduce cytopathic effects associated with viral infection and provide heightened expression of nucleic acid segment inserts.

A phosphatidylinositol turnover assay was performed on neuronal cells infected with each of vTKhm1-1, vTKhm1-2, and vTKhm1-3. This assay demonstrates that the m1AchR function to stimulate second messenger systems. 10 d cultures of mouse cortical neurons were infected or mock-infected and then incubated prior to measurement of PI turnover using 1 uCi/ml [$^3$H] inositol in inositol-free minimal essential medium. Cultures were washed 3× in Hanks buffered saline solution. Cells were treated or mock-treated with 1 mM carbachol. After 45 min, the medium was removed, cells were washed once with HBSS, cold 3% perchloric acid was added, and inositol phosphate levels were determined exactly as described previously (Murphy et al., *FASEB J.* 4:1624–1633, 1990). Second messengers were stimulated 5 fold by 12 hpi in infected Vero cells. Second messengers were stimulated 4 fold in rat cortical neurons.

EXAMPLE 8

Generation of a Recombinant Herpesvirus Vector which Espresses an Antisense 5-HT2a Receptor Sequence A. Materials and Construction Methods 1. Vector Construction Plasmid pTKSR2(−) (which is based on pUC19) consists of a Cytomegalovirus (CMV) immediate early promoter, an entire coding region of rat 5-HT2 receptor gene in an antisense orientation (see Julius et al., PNAS 87:928–932, 1990; see also Genbank Accession No. M30105), and a poly A sequence from the bovine growth hormone gene. The promoter-antisense 5-HT2 receptor gene sequence and poly A region is framed by a Pvu II fragment of the HSV-1 tk gene.

A HSV-1 kos mutant strain vhs A was utilized for construction of recombinant virus. Briefly, in vhs A, a genome region responsible for shutting off host-cell macromolecules synthesis has been deleted. The virus was propagated in African Green Monkey kidney cells (Vero, ATCC Accession No. CRL 1587) cultured with MEM medium with 10% fetal bovine serum (Gibco BRL) at 37° C. and 10% $CO_2$.

The recombinant virus was constructed using homologous recombination described above. Briefly, viral DNA from vhs A and pTKSR2(−) plasmid DNA were cotransferred into Vero cells utilizing calcium phosphate precipitation. One hundred micrograms of broma-D-oxycytidine (Sigma) was added to the culture to select for tk(−) virus. Generated virus was collected and diluted with medium to infect Vero cells in 96-well dishes. After 48 hours, medium containing released virus and cellular debris from the 96 wells were blotted on a membrane followed by a hybridization with a $^{32}$p labelled probe made from the 5-HT2 receptor gene. Virus from positive wells were then plaque purified three times and insertion of the antisense construct was confirmed by Southern blotting and DNA polymerase chain reaction.

2. Preparation of Neuronal Cultures

Rat primary cortical cultures were prepared from postnatal day 1 Long-Evans rats. Briefly, each rat was sacrificed by decapitation under halothane anesthesia. The cerebral cortices were dissected and minced with iridectomy scissors into fine fragments in a brain dissecting buffer solution containing $Ca_2^+/Mg_2^+$ free Hank's Balanced Salt Solution (HBSS, Gibco). The fragments were transferred into 3 ml of a solution with 0.16% trypsin (Sigma) and 0.03% DNase I (Boehringer Mannheim) at 37° C. for 10 minutes. The tissue was then gently dissociated with a 5 ml plastic pipette followed by addition of 2 ml ice cold fetal bovine serum to stop the trypsin activity. The cell suspension was centrifuged and the cell pellets were resuspended in MEM supplement with 4 mM L-glutamine, 16 mM $NaHCO_3$, 20 mM HEPES and 10% FBS. After two washes with fresh medium, $2\times10^6$ cells in 2 ml medium were plated onto poly-L-lysine pretreated glass coverslips in 35 mm dishes. The culture was incubated in a 5% $CO_2$ incubator at 37° C. The medium was replaced on the following day with fresh medium containing 20 mM cytosine arabinofuranoside (Ara-C, Sigma) to inhibit the proliferation of nonneuronal cells.

3. RNase Protection Assay

Two RNA probes were generated by in vitro transcription. Briefly, probe A was 600 nt with a sequence identical to 5' end sense strain of rat 5-HT2a receptor gene. Probe B was 620 nt in length and spans a region including 300 nt sequence of CMV promoter followed by the first 320 nt sequence of 3' end rat 5-HT2a receptor gene. An RNase protection kit was used and the assay was carried out following the manufacturer's instruction. The digested hybridized probes were run on 5% Acrylamide gel and exposed on film overnight.

4. Ligand Binding Assays

Cells from primary cortical cultures were collected and were freezed-thawed three times before being used for the ligand assays. $10^6$ cells were incubated with 1nM[$^3$H] ketanserin hydrochloride (85.1 Ci/mmol) or 5nM[$^3$H] mesulergine (Amersham, 750 Ci/mmol) (both from NEN, Du Pont) or 4.5 nM[$^3$H]N-methyl-scopolamine (NMS, 75 Ci/mmol) in Tris buffer (170 mM, pH 7.5) for one hour at room temperature. The non-specific bindings in these assays were less than 20% determined by adding 2,000-fold concentrations of non-isotope-labelled same ligands into the corresponding incubation solutions. Following the incubation, the cells were washed 3×5 min in the same buffer at 4° C. and resuspended in 1 ml of Formula 963 (NEN) for counting of radioactivity in a Beckman LS 2800 liquid scintillation counter.

B. Results

The recombinant virus, vTKSR2(−), containing an antisense construct for the rat 5-HT gene was used to infect Vero cells at multiplicity of infection (moi)=3. Total RNA from the infected cells was collected at 7, 17 and 24 hours postinfection. Probe A gave rise to a protected band which equals to the full length of the probe while probe B was only partially protected and gave rise to a band of 320 nt, the size of transcribed portion. The amount of antisense transcripts increased with the time of postinfection up to 17 hours and declined thereafter.

To prove that the transcribed antisense MRNA could block the expression of endogenous 5-HT2a receptors in neurons, primary cultures of rat cerebral cortex were used for ligand binding assays following the viral infections. At 7 hours postinfection of vTKSR2(−)(moi=3), the neuronal cultures were double labelled with a monoclonal antibody against microtubule-associated protein type 2 (MAP-2), a neuron-specific marker, and a polyclonal antibody against HSV-1 virus. More than 90% of cells in the cultures were labelled by MAP-2 antibody indicating their neuronal nature. Among the MAP-2 positive cells, more than 80% of them were also showed immunoreactivity of HSV-1 antigens, indicating that a large population of the neurons were infected by the recombinant virus. Following the infection with vTKSR2(−) or the parental virus vhs A at moi=3, neurons were incubated with [$^3$H]ketanserin or [$^3$H] NMS at either 7 hours, 17 hours and 48 hours postinfection. The radioactivity of bound [$^3$H]ketanserin was significantly reduced in cultures infected with vTKSR2(−) comparing to the VHS A infected ones. The reduction of binding in neuronal cultures peaked at 17 hours and declined in 48 hours postinfection. In contrast, there was no difference in binding of [$^3$H]NMS between the vTKSR2(−) and VHS A infected cultures. Furthermore, using [$^3$H]mesulergine, a ligand more specific for 5-HT2c receptors, to label the infected cultures, a minor reduction of binding was observed with a marginal significance of statistics.

EXAMPLE 9

In Vivo Administration

Figure 12A:
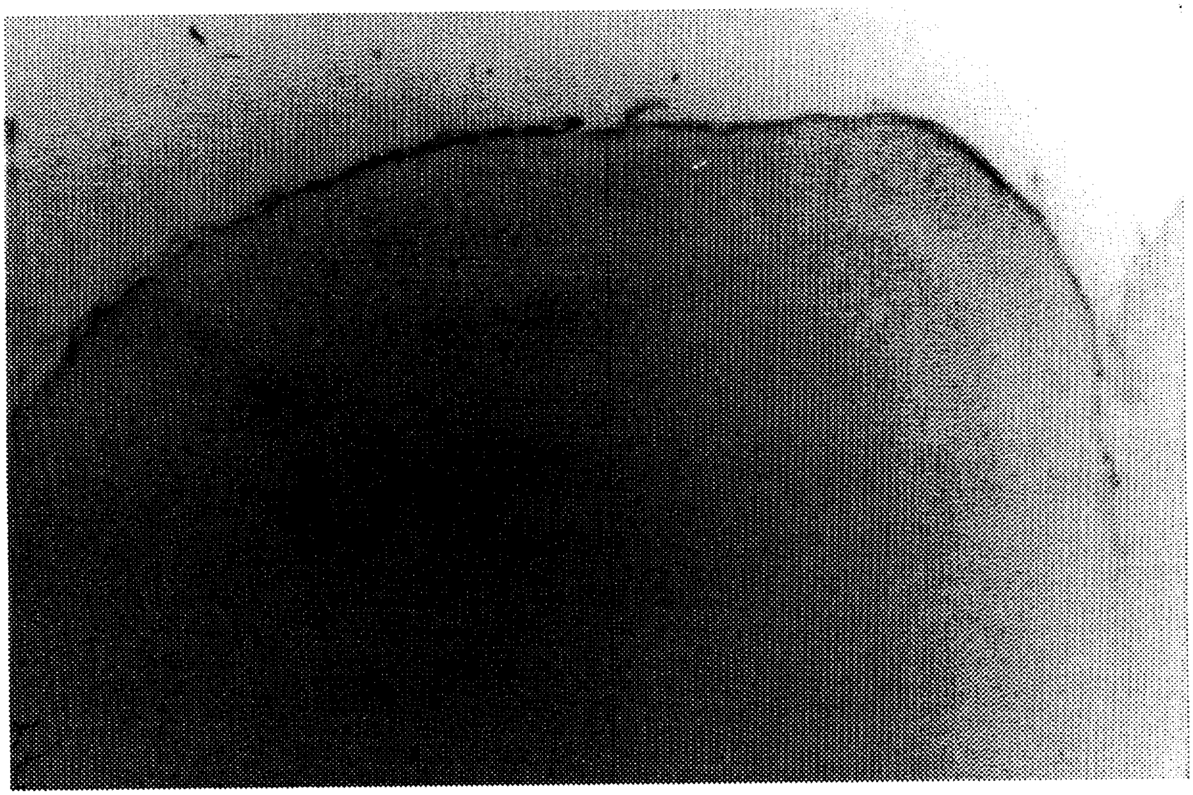
FIGS. 12A and 12B are two photographs of sections of rat brains which have been infected with a recombinant Herpesvirus.
Figure 12B:
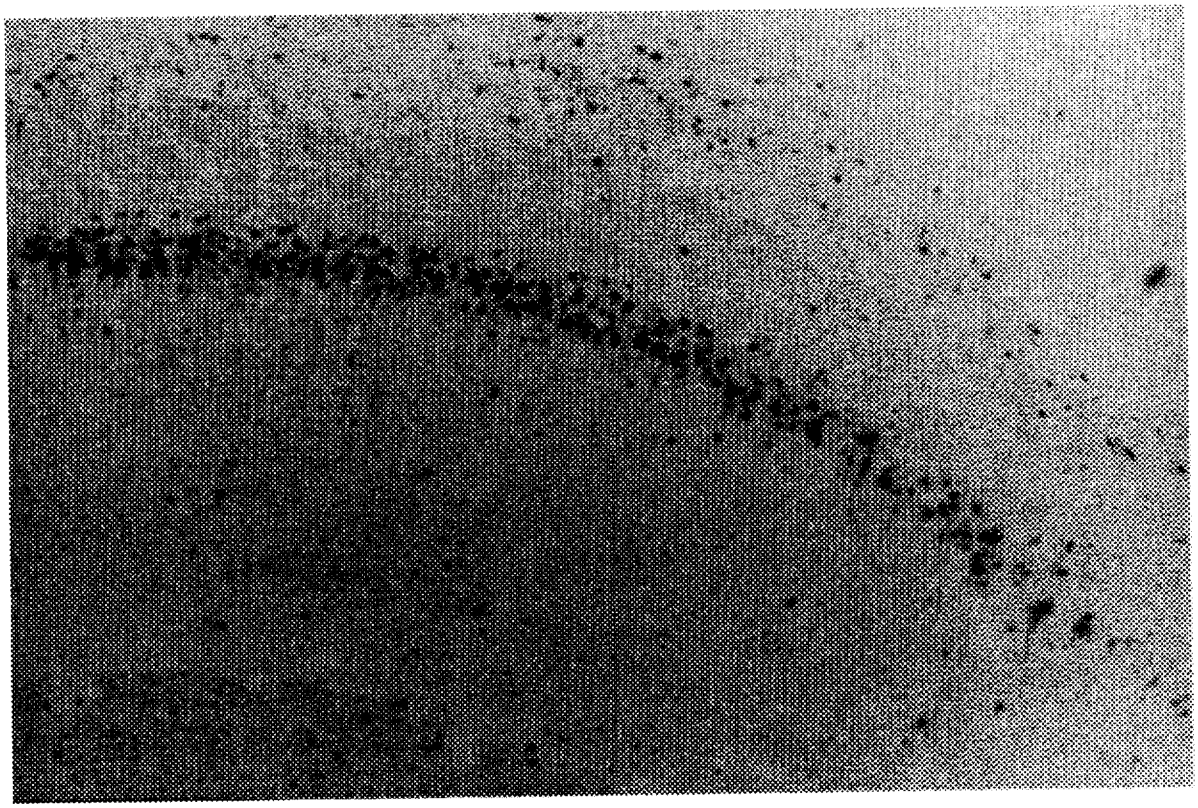

Long-Evan's rats were utilized as subjects to determine the degree of infectivity of recombinant Herpesvirus vectors. Briefly, the rats were anesthetized with an intraperitoneal injection of sodium pentobarbitol (Somnotol, 40 mg/kg), and placed into a stereotaxic apparatus. A craniotomy was performed over the appropriate brain structure, and the Herpesvirus vector 5HT2 described above in Example 8 was injected. In the case of one rat, a total of 10 ul at a titer of $10^8$ pfu/ml was injected into the hippocampus over a period of 20 minutes. The rat was then sutured and treated with a topical antibiotic (chloramphenicol, 1%). After 4 days, the rat was sacrificed and the hippocampal region sectioned and stained with an immunohistochemical to recognize the viral envelope. The results are shown in FIG. 12B. Briefly, infection can be seen in a substantial number of cells within the needle track.

Another rat was injected in the cortex with 200 ul at a titer of $5\times10^7$ pfu/ml over a period of 90 minutes. As above, the rat was then sutured and treated with a topical antibiotic. After 2 days the rat was sacrificed and the cortex sectioned and stained. Results are shown in FIG. 12A. Briefly, strong labelling (and thus, infection of cells) can be seen throughout the periphery of the cortex.

EXAMPLE 10

Construction and Assay of Neuron-Specific Vectors

A. Materials and Construction Methods

All restriction endonucleases, media, fetal bovine serum (FBS), nerve growth factor (NGF) and fine chemicals were obtained from GIBCO BRL Life Technologies Inc. (Burlington, Ontario). Unless otherwise noted, cloning procedures followed standard procedures (Sambrook et al., "Molecular Cloning: A laboratory manual," 2nd ed., Cold Spring Harbor Laboratory Press, Cold Spring Harbor, N.Y.).

Figure 13:
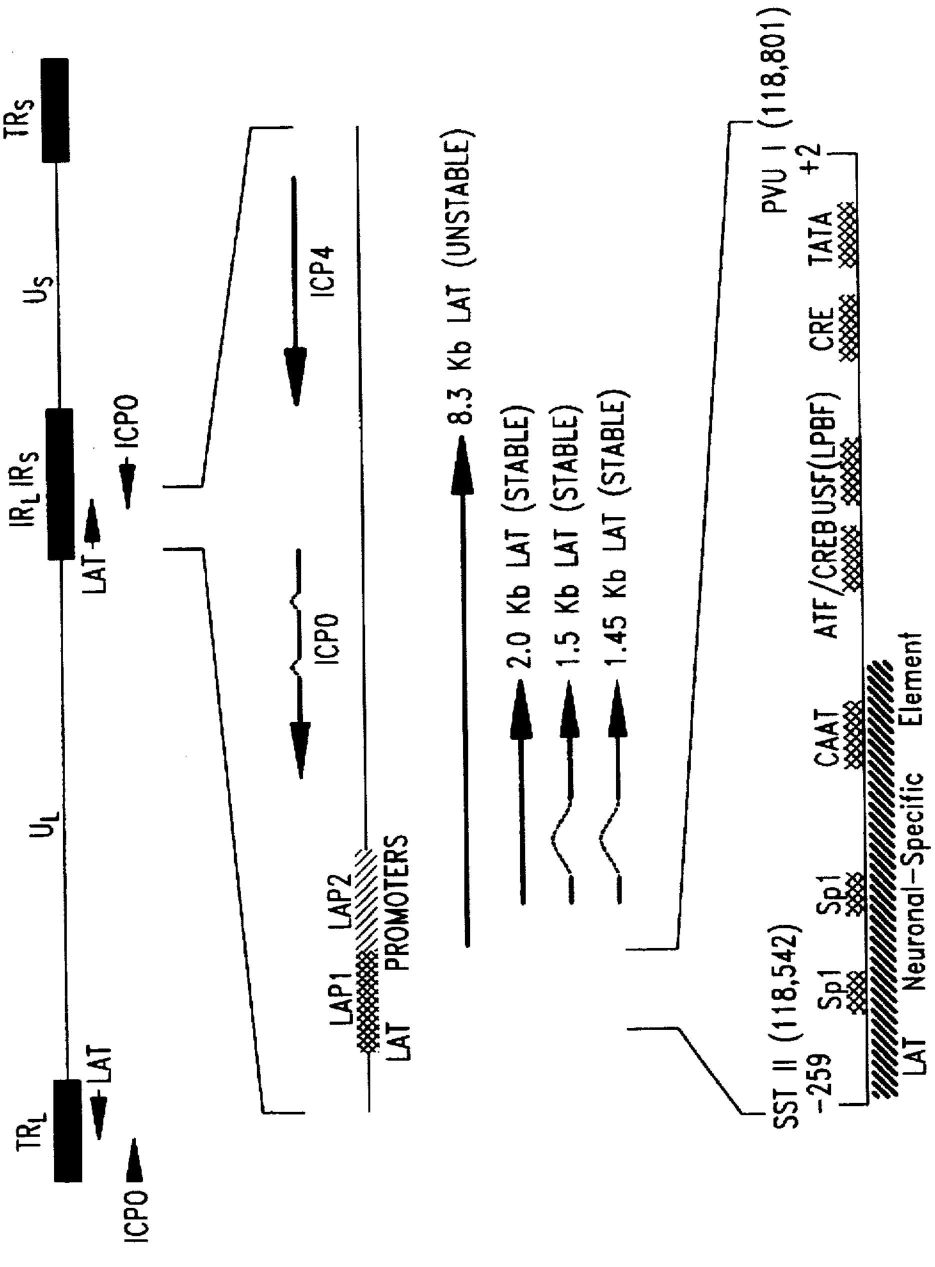
FIG. 13 is a schematic illustration of the LAT promoters within an HSV-1 transcript. Briefly, $U_L$, $U_S$, $TR_L$, $TR_S$, $IR_L$ and $IR_S$, represent HSV-1 genomic sequences corresponding to unique-long, unique-short, terminal repeat-long, terminal repeat-short, inverted repeat-long and inverted repeat-short, respectively. Lines with arrowheads denote HSV-1 RNA transcripts. LAT promoters are designated as LAP1 and LAP2. All cis transcription regulatory elements represented on the LAP1 promoter region from +2 to −259 (118,542 to 118,801 according to McGeoch et al., *J. Gen. Virol.* 69:1531–1574, 1988).

Plasmid p0N134 contains the HSV-1 (strain KOS) latency-associated transcript promoter (LAP1) (Selden et al., *Mol. Cell. Biol.* 6:3173–3179, 1986; Ho and Mocarski, *Proc. Nat'l Acad. Sci USA* 86:7596–7600, 1989). Briefly, the LAP1 promoter is located immediately upstream of the large primary approximately 8.5kb LAT RNA transcript and about 650 bp upstream of the 5' ends of the small LAT RNAs. As shown in FIG. 13, this promoter contains a typical TATA box and several characteristic eukaryotic transcription regulatory elements, such a cyclic AMP-response elements, a CATT box, and two Spl sites. One region of the LAP promoter (between about −161 and about −259) is particularly preferred for conferring a neuronal cell-type specific activity.

The LAP1 promoter was cloned from p0N134 by digestion of the plasmid with PvuI and a 609 bp DNA fragment containing the LAP1 promoter from +2 to −608 (Batchelor and O'Hare, *J. Virol.* 66:3573–3582, 1992; McGeoch et al., *J. Gen. Virol.* 69:1531–1574, 1988) was inserted at the Hinc II site of the pBluescript KS (+) vector (Stratagene, LaJolla, Calif.). The minimum LAP1 promoter used in this study was constructed by a further SstII deletion of the upstream sequences at −259.

Dimer neuronal restrictive silencer elements were constructed by annealing two synthetic oligonucleotides essentially as described by Mori et al. (*Neuron* 9:45–54, 1992), S36A: CAAAGCCATT TCAGCACCAC GGAGAGTGCC TCTGC (Sequence I.D. No. 2) and S36B: GCAGAGGCAC TCTCCGTGGT GCTGAAATGG CTTTG (Sequence I.D. No. 3), followed by ligating the double-stranded DNA fragments and inserting them into a pBluescript KS(+) vector at the HincII site. The correct sequences and orientations of dimer silencers were examined and verified by standard double-stranded dideoxynucleotide sequencing.

The human cytomegalovirus (hCMV) major immediate early gene enhancer from −113 to −601 (Boshart et al., *Cell* 41:521–530, 1985) was cloned from pRc/CMV (Invitrogen, San Diego, Calif.) by digestion of the hCMV major immediate early promoter with BanI and HincII so that the TATA box of the promoter was deleted. The 488 bp enhancer fragment was inserted at the HincII site of pBluescript KS(+).

A 21kb BamHI-EcoRI human growth hormone (hGH) gene fragment including its own polyadenylation signal was cloned out from a plasmid p0GH (Selden et al., *Mol. Cell. Biol.* 6:3173–3179, 1986).

B. Cells, Transfections and hGH Assay

Vero and rat pheochromocytoma (PC12) cells were obtained from the ATCC. Briefly, Vero cells are monkey kidney cells which are capable of supporting HSV-1 propagation in vitro. PC12 cells are neural crest derived rat phaeochromocytoma cell line. In response to nerve growth factor, PC12 cells stop dividing and differentiate into neuron-like cells with many properties characteristic of peripheral nervous tissue.

Vero cells were propagated in Dulbecco's Modified Eagle Medium (DMEM) with 10% FBS and 10% inactive horse serum. Differentiation of PC12 cells induced by NGF at a concentration of 150 ng/ml was performed at 16 hours post-transfection. Transfection of Vero and PC12 cells with the plasmid constructs on six-well dishes with $3\times10^5$ cells per well was performed utilizing the calcium phosphate-mediated precipitation method essentially as described by Sambrook et al., supra. The amount of DNA used in the transfection was titrated to 5 ug per well. The linear response range of hGH accumulated in the medium was determined between 48 to 96 hours after transfection for both cell types and therefore, the media were collected at 48, 72 and 96 hours after transfection. The amount of hGH secreted into the medium was measured with a solid-phase two-site radioimmunoassay kit under the conditions recommended by the manufacture (Nichols Institute Diagnostics, Los Angeles, Calif.). Data were collected from at least two sets of transfection experiments and each transfection was performed in triplicates.

C. Chimeric Expression Cassettes with LAP1 Promoters and NRSE Silencer Elements

Figure 14B:
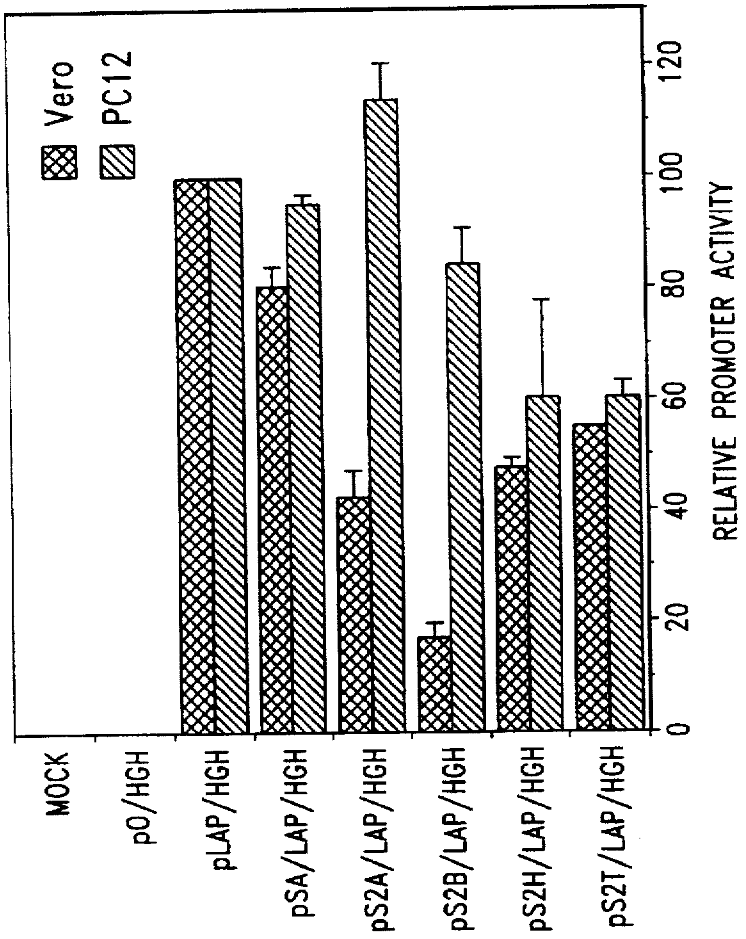
FIGS. 14A and 14B are graphs which show the schematic construction and relative activity in neural and non-neural cells of chimeric expression cassettes containing LAP1 promoters combined with NRSE silencer elements.
Figure 14A:
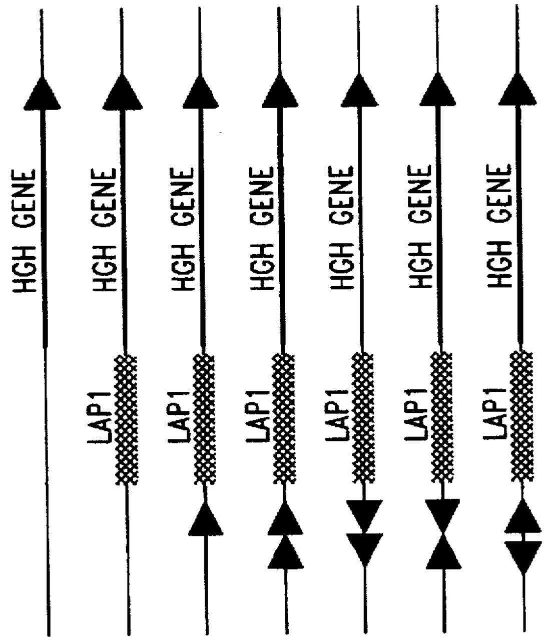

To selectively alter LAP1 promoter activity only in neuronal cells, several synthetic NRSE dimers were placed upstream of the LAP1 promoter in all possible orientations (FIG. 14A) and tested in both Vero and PC12 cells by transient expression assays. As shown in FIG. 14B, the NRSE monomer (pSA/LAP/HGH) suppressed the LAP1 promoter activity by only 20% in Vero cells and had no effect on the promoter activity in PC12 cells as compared to the LAP1 promoter without NRSE (pLAP/HGH). Moreover, when the chimeric LAP1 promoters with the head-to-tail NRSE dimers in either orientation (pS2A/LAP/HGH and pS2B/LAP/HGH) were introduced into Vero cells, the promoter activity decreased to 60 to 80% relative to the parental plasmid construct (pLAP/HGH). These NRSE dimers however, did not inhibit LAP1 promoter activity in PC12 cells. In addition, chimeric LAP1 promoters with either head-to-head or tail-to-tail NRSE dimers (pS2H/LAP/HGH and pS2T/LAP/HGH) showed somewhat lower promoter activity (about 60%) as compared to the construct without NRSE and had no cell-type preference for Vero or PC12 cells. From these results it was concluded that an NRSE element efficiently suppressed the HSV-1 LAP1 promoter in non-neuronal cells and an NRSE dimer was more effective than a monomer when placed in a head-to-tail orientation. Therefore, the chimeric promoter construct pS2B/LAP/HGH was chosen for further experiments.

Figure 15B:
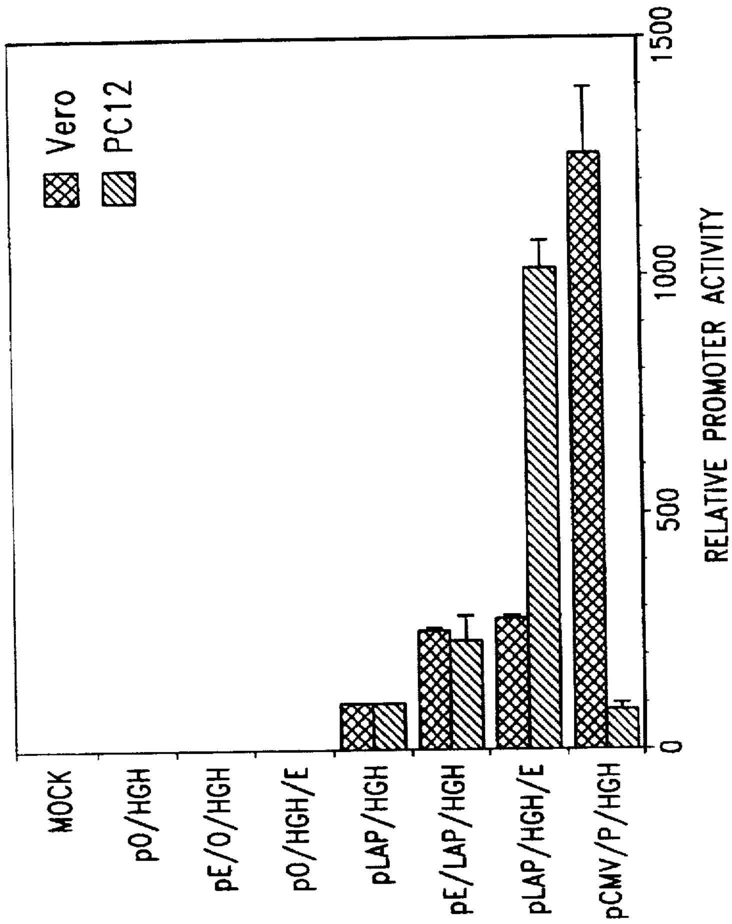
FIGS. 15A and 15B are graphs which show the schematic construction and relative activity in neural and non-neural cells of several different chimeric expression cassettes containing a LAP1 promoter and hCMV enhancer.
Figure 15A:
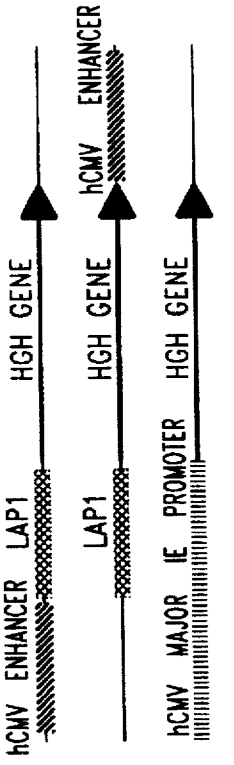

The hCMV enhancer element from −113 to −601 of the hCMV major IE promoter was placed either upstream of the LAP1 promoter (pE/LAP/HGH) or at the 3' end of the hGH reporter gene (pLAP/HGH/E). The resulting chimeric promoter constructs were introduced into both Vero and PC12 cells. As shown in FIG. 15B, the LAP1 promoter activity was stimulated by the enhancer in both cell types as compared to the basal level activity of the basic LAP 1 promoter construct pLAP/HGH in each cell line, which indicates that the enhancer element worked in both cell types. Moreover, in Vero cells, the LAP1 promoter activity was up-regulated by about 2.5 fold regardless of the position of the enhancer. By contrast, in PC12 cells, when the hCMV enhancer was placed at the 3' end of the hGH gene (pLAP/HGH/E), the enhancer activity was five times higher than when the enhancer was upstream of the LAP1 promoter (pE/LAP/HGH).

To evaluate the potential cell-type preference contributed by different promoters, the hCMV major immediate early (IE) promoter with its own enhancer was included as a control. As shown in FIG. 15B, in Vero cells the hCMV major IE promoter itself had a much higher activity (fourteen fold) than the LAP1 promoter, whereas in PC12 cells it had the same activity as the LAP1 promoter. These results suggest that the relative hCMV enhancer activity in different cell types was well dependent on the promoter to which it was linked. In addition, since the enhancer element itself showed no promoter activity in either Vero or PC12 cells, the chimeric LAP 1 promoter must have been enhanced as a result of interactions between the LAP 1 promoter and the hCMV enhancer element. These results demonstrated that the HSV-1 LAP1 promoter could be up-regulated in both neuronal and non-neuronal cells by an enhancer from the hCMV major IE promoter. However, the level of enhancement of the LAP1 promoter in neuronal cells was dependent on the position of the enhancer element relative to the promoter.

In summary, the HSV-1 LAP1 promoter can be regulated by other gene regulatory sequences either to suppress the promoter activity in non-neuronal cells, or to enhance its activity in both neuronal and non-neuronal cells.

Figure 16B:
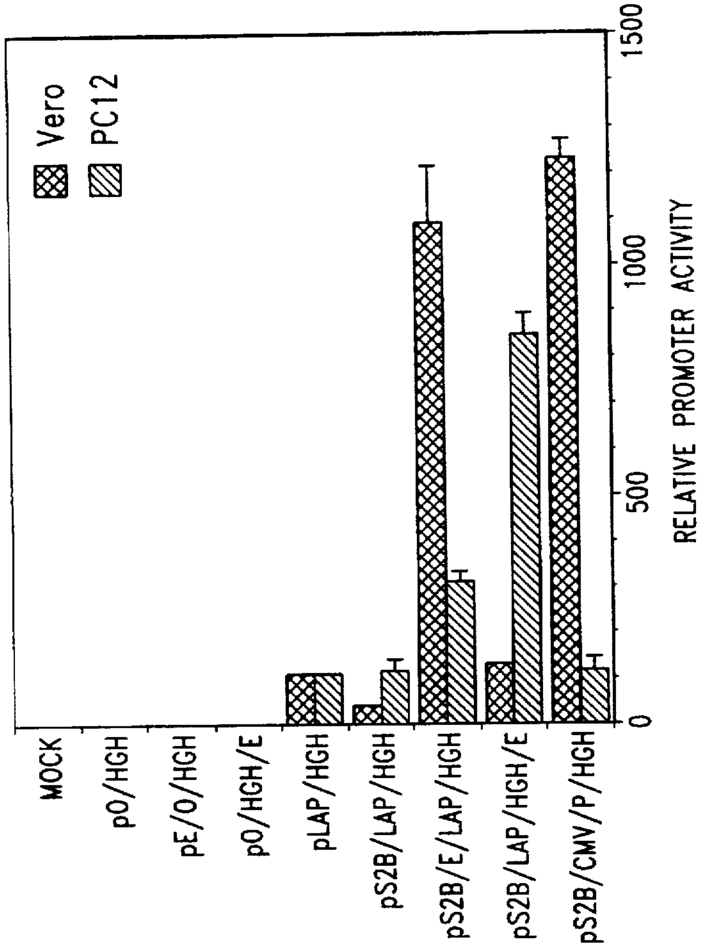
FIGS. 16A and 16B are graphs which show the schematic construction and relative activity in neural and non-neural cells of several different chimeric expression cassettes containing LAP1 promoters combined with both NRSE silencer elements and the hCMV enhancer.
Figure 16A:
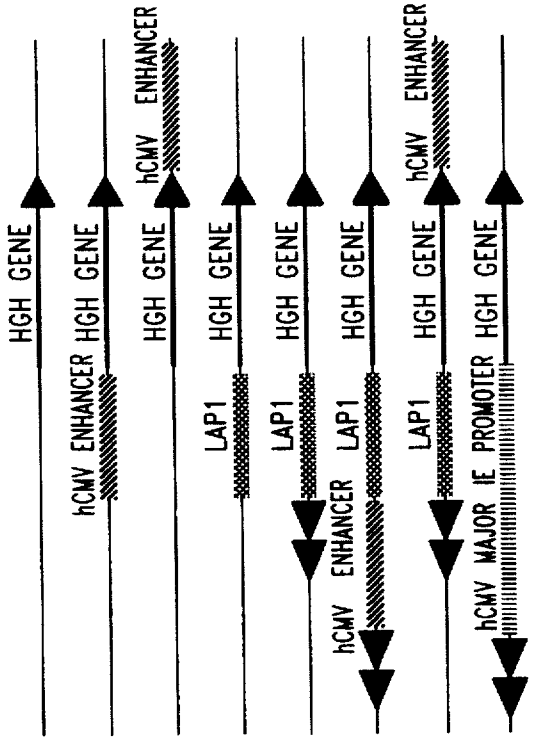

D. Chimeric Expression Cassettes with LAP1 Promoters, NRSE Silencer Elements and hCMV Enhancers The chimeric LAP1 promoter construct containing the silencer dimer, pS2B/LAP/HGH, was used as a backbone for further studies. Briefly, this construct contained a head-to-tail NRSE dimer upstream of the LAP1 promoter and had the lowest promoter activity among the constructs tested in Vero cells (FIG. 14B). The hCMV enhancer element was added either upstream of the LAP1 promoter (pS2B/E/LAP/HGH), or at the 3' end of the hGH reporter gene (pS2B/LAP/HGH/E), as shown in FIG. 16A. When pS2B/E/LAP/HGH and pS2B/LAP/HGH/E constructs were introduced into Vero and PC12 cells, they all showed a higher level of promoter activity in both cell types than the construct pS2B/LAP/HGH, which lacks the enhancer element. Moreover, in Vero cells, the NRSE dimer no longer suppressed the LAP1 promoter activity in the presence of the enhancer (FIG. 16B). Thus, the hCMV enhancer activity was dominant over the silencing activity of the NRSE dimer element when they were combined. Interestingly, the enhancer also showed position effects on the LAP1 promoter activity in the presence of the NRSE dimer. When it was placed at the 3' end of the hGH reporter gene (pS2B/LAP/HGH/E), it showed a stronger enhancement of the LAP1 promoter in PC12 cells than in Vero cells as demonstrated previously (FIG. 15B). By contrast, when it was placed at the 5' end of the LAP1 promoter (pS2B/E/LAP/HGH), it showed an unusually high level of activity in Vero cells, whereas in PC12 cells it showed only slight enhancing activity.

E. The Chimeric LAP1 Promoter Activity in the Differentiated PC12 Cells Induced by NGF Nerve growth factor (NGF) is important for the maintenance of neuronal cell survival. In the presence of NGF, PC12 cells undergo various physiological changes and differentiate into neuron-like cells with many characteristics of peripheral nervous tissue.

Figure 17B:
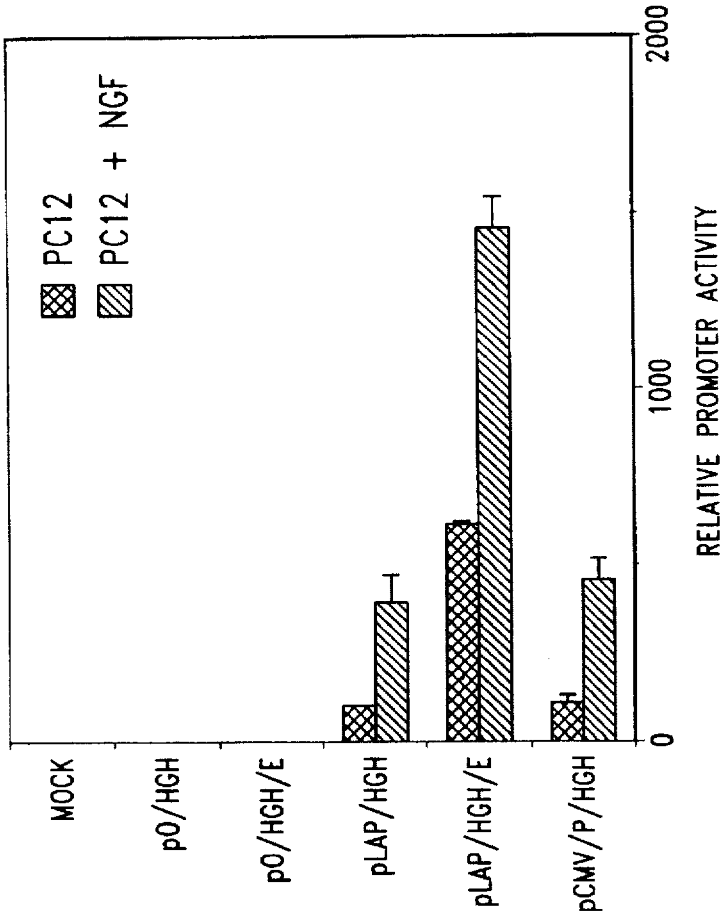
FIGS. 17A and 17B are graphs which show the schematic construction and relative activity in neural and non-neural cells of several different chimeric expression cassettes containing chimeric LAP1 promoters in differentiated PC 12 cells.
Figure 17A:
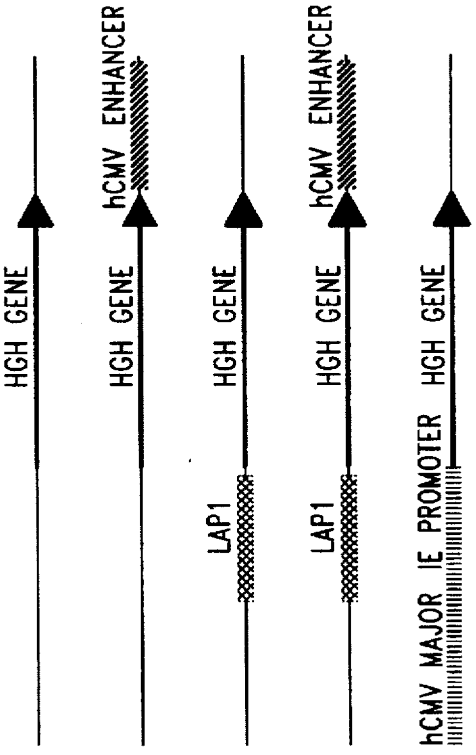

In order to test the responses of LAP1 promoters in NGF induced PC12 cells, chimeric LAP1 promoter constructs were first transfected into PC12 cells and then cell differentiation was induced by treatment with NGF. As shown in FIG. 17B, the LAP1 promoter activity increased about four fold in response to NGF, whereas the chimeric LAP1 promoter with the hCMV enhancer element (pLAP/HGH/E) showed two fold increased activity. Interestingly, the hCMV major IE promoter also increased its activity to the same extent as the LAP1 promoter in response to NGF treatment in PC12 cells, which suggests that the up-regulation of the LAP1 promoter in the differentiated PC12 cells was part of an overall stimulation of transcription in response to NGF.

From the foregoing, it will be evident that although specific embodiments of the invention have been described herein for the purposes of illustration, various modifications may be made without deviating from the spirit and scope of the invention.

We claim:

1. An expression cassette capable of expressing a sequence of interest, comprising one or more neuronal specific silencer elements, a promoter element operably linked to a sequence of interest, and an enhancer, wherein said enhancer and silencer elements are positioned such that they are not adjacent to one another.

2. The expression cassette according to claim 1 wherein said silencer element is a neuronal restrictive silencer element.

3. The expression cassette according to claim 1 wherein said promoter element is selected from the group consisting of CMV, SV40, herpes promoters and adenovirus promoters.

4. An expression cassette, comprising a LAT promoter element operably linked to a sequence of interest, followed by an enhancer.

5. The expression cassette according to claim 4, further comprising a neuronal-specific silencer element, wherein said enhancer and silencer elements are positioned on said vector such that they are not adjacent to one another.

6. The expression cassette according to claim 5 wherein said neuronal-specific silencer element is a neuronal-restrictive silencer element.

7. The expression cassette according to claim 1 or 4 wherein said sequence of interest is selected from the group consisting of antisense sequences, genes which encode disease-associated antigens, genes which encode immunologically active molecules, replacement genes, and genes which encode toxic proteins.

8. A gene delivery construct which contains an expression cassette according to any one of claims 1–7.

9. The gene delivery construct according to claim 8 wherein said construct is a HSV-1 vector.

10. A host cell which contains an expression cassette according to any one of claims 1–7.

11. A method for producing a protein, comprising:

(a) introducing an expression cassette according to any one of claims 1–7 which directs the expression of a protein of interest, or a gene delivery construct according to claim 8, into a host cell; and (b) culturing said host cell under conditions, and for a time sufficient, to permit expression of said protein.

12. The method of claim 11, further comprising the step of purifying said protein.

13. A method for introducing a selected sequence of interest into an in vitro culture containing neuronal cells, comprising introducing an expression cassette according to any one of claims 1–7, or a gene delivery construct according to claim 8, into an in vitro culture containing neuronal cells.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( x i ) SEQUENCE DESCRIPTION: SEQ ID NO:1:

NNNBNGUCNN NNNNNN 16

( 2 ) INFORMATION FOR SEQ ID NO:2:

( i ) SEQUENCE CHARACTERISTICS:
( A ) LENGTH: 35 base pairs
( B ) TYPE: nucleic acid
( C ) STRANDEDNESS: single
( D ) TOPOLOGY: linear ( x i ) SEQUENCE DESCRIPTION: SEQ ID NO:2:

CAAAGCCATT TCAGCACCAC GGAGAGTGCC TCTGC 35

( 2 ) INFORMATION FOR SEQ ID NO:3:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:3:

GCTGAAATGG CTTTG 15